US011103652B2

(12) United States Patent
Yudelevich et al.

(10) Patent No.: US 11,103,652 B2
(45) Date of Patent: Aug. 31, 2021

(54) THREE POSITION NEEDLE RETRACTION

(71) Applicant: West Pharma. Services IL, Ltd., Ra'anana (IL)

(72) Inventors: Michael Yudelevich, Winnipeg (CA); Yossi Bar-El, Beit Arye (IL); Gil Yigal, Gan Yavne (IL); Reuven Y. Filman, Tel Mond (IL)

(73) Assignee: WEST PHARMA. SERVICES IL, LTD., Ra'anana (IL)

(*) Notice: Subject to any disclaimer, the term of this patent is extended or adjusted under 35 U.S.C. 154(b) by 163 days.

(21) Appl. No.: 16/302,470

(22) PCT Filed: Jun. 1, 2017

(86) PCT No.: PCT/US2017/035486
§ 371 (c)(1),
(2) Date: Nov. 16, 2018

(87) PCT Pub. No.: WO2017/210448
PCT Pub. Date: Dec. 7, 2017

(65) Prior Publication Data
US 2019/0160230 A1 May 30, 2019

Related U.S. Application Data

(60) Provisional application No. 62/344,782, filed on Jun. 2, 2016.

(51) Int. Cl.
*A61M 5/32* (2006.01)
*A61M 5/142* (2006.01)
*A61M 5/20* (2006.01)

(52) U.S. Cl.
CPC .......... *A61M 5/3232* (2013.01); *A61M 5/321* (2013.01); *A61M 5/322* (2013.01);
(Continued)

(58) Field of Classification Search
CPC .... A61M 5/322; A61M 5/3219; A61M 5/321; A61M 5/3205; A61M 5/3287;
(Continued)

(56) References Cited

U.S. PATENT DOCUMENTS 3,782,365 A 1/1974 Pinna
4,026,128 A 5/1977 Blanco
(Continued)

FOREIGN PATENT DOCUMENTS

CN 1636605 A 7/2005
CN 1747683 A 3/2006
(Continued)

OTHER PUBLICATIONS

Office Action dated Sep. 30, 2020 in Chinese Application No. 20170033863.0.

*Primary Examiner* — Nathan R Price
*Assistant Examiner* — Anna E Goldberg-Richmeier
(74) *Attorney, Agent, or Firm* — Panitch Schwarze Belisario & Nadel LLP

(57) ABSTRACT

In some embodiments a system and method are described for safeguarding a hazard, the hazard, for example a needle point, may be moved between a protected retracted position, an active extended position and/or an intermediate position. Optionally in the retracted position, the hazard may be protected inside a housing. Optionally in the extended position, the hazard may be exposed. Optionally, in the intermediate position the hazard may be partially protected and/or concealed, for example by a shield and/or in an indentation. In some embodiments, compromising a shield causes the hazard to be retracted to the retracted position.

12 Claims, 31 Drawing Sheets

(52) U.S. Cl.
CPC ....... *A61M 5/3205* (2013.01); *A61M 5/14244* (2013.01); *A61M 5/3219* (2013.01); *A61M 2005/206* (2013.01)

(58) Field of Classification Search
CPC ........ A61M 5/3232; A61 2005/1585; A61M 2005/14252; A61M 2005/14256; A61M 2005/1426; A61 2005/206
See application file for complete search history.

(56) References Cited

U.S. PATENT DOCUMENTS

| | | | |
|---|---|---|---|
| 4,919,596 | A | 4/1990 | Slate et al. |
| 5,348,544 | A | 9/1994 | Sweeney et al. |
| 5,482,446 | A | 1/1996 | Williamson et al. |
| 5,496,274 | A | 3/1996 | Graves et al. |
| 5,562,686 | A | 10/1996 | Sauer et al. |
| 5,658,133 | A | 8/1997 | Anderson et al. |
| 5,672,160 | A | 9/1997 | Osterlind et al. |
| 5,814,020 | A | 9/1998 | Gross |
| 5,868,710 | A | 2/1999 | Battiato et al. |
| 5,941,850 | A | 8/1999 | Shah et al. |
| 6,558,365 | B2 | 5/2003 | Zinger et al. |
| 6,632,201 | B1 | 10/2003 | Mathias et al. |
| 6,972,002 | B2 | 12/2005 | Thorne |
| 7,097,637 | B2 | 8/2006 | Triplett et al. |
| 7,704,229 | B2 | 4/2010 | Moberg et al. |
| 8,152,779 | B2 | 4/2012 | Cabiri |
| 8,348,898 | B2 * | 1/2013 | Cabiri ............... A61M 5/14248 604/137 |
| 8,915,882 | B2 | 12/2014 | Cabiri |
| 9,072,827 | B2 | 7/2015 | Cabiri |
| 9,149,575 | B2 | 10/2015 | Cabiri |
| 9,242,044 | B2 * | 1/2016 | Markussen ......... A61M 5/3234 |
| 9,393,365 | B2 | 7/2016 | Cabiri |
| 9,492,610 | B2 | 11/2016 | Cabiri |
| 9,511,190 | B2 | 12/2016 | Cabiri |
| 9,522,234 | B2 | 12/2016 | Cabiri |
| 10,071,196 | B2 * | 9/2018 | Cabiri ............... A61M 5/14248 |
| 2002/0055711 | A1 | 5/2002 | Lavi et al. |
| 2002/0065488 | A1 | 5/2002 | Suzuki et al. |
| 2003/0135159 | A1 | 7/2003 | Daily et al. |
| 2003/0199827 | A1 | 10/2003 | Thorne |
| 2004/0010207 | A1 | 1/2004 | Flaherty et al. |
| 2004/0158172 | A1 | 8/2004 | Hancock |
| 2004/0186424 | A1 | 9/2004 | Hjertman |
| 2005/0049553 | A1 | 3/2005 | Triplett et al. |
| 2005/0159706 | A1 | 7/2005 | Wilkinson et al. |
| 2006/0173410 | A1 | 8/2006 | Moberg et al. |
| 2006/0195029 | A1 | 8/2006 | Shults et al. |
| 2007/0016381 | A1 | 1/2007 | Kamath et al. |
| 2007/0106218 | A1 | 5/2007 | Yodfat et al. |
| 2007/0167912 | A1 | 7/2007 | Causey et al. |
| 2008/0195049 | A1 | 8/2008 | Thalmann et al. |
| 2008/0208138 | A1 | 8/2008 | Lim et al. |
| 2008/0215015 | A1 | 9/2008 | Cindrich et al. |
| 2008/0249473 | A1 | 10/2008 | Rutti et al. |
| 2008/0269687 | A1 | 10/2008 | Chong et al. |
| 2008/0275407 | A1 | 11/2008 | Scheurer |
| 2009/0043253 | A1 | 2/2009 | Podaima |
| 2009/0054852 | A1 | 2/2009 | Takano et al. |
| 2009/0062767 | A1 | 3/2009 | Van Antwerp et al. |
| 2009/0076360 | A1 | 3/2009 | Brister et al. |
| 2009/0139724 | A1 | 6/2009 | Gray et al. |
| 2009/0216103 | A1 | 8/2009 | Brister et al. |
| 2010/0137831 | A1 | 6/2010 | Tsals |
| 2010/0152658 | A1 | 6/2010 | Hanson et al. |
| 2010/0162548 | A1 | 7/2010 | Leidig |
| 2010/0274202 | A1 | 10/2010 | Hyde et al. |
| 2011/0125056 | A1 | 5/2011 | Merchant |
| 2011/0144584 | A1 | 6/2011 | Wozencroft |
| 2011/0160655 | A1 | 6/2011 | Hanson et al. |
| 2012/0022344 | A1 | 1/2012 | Kube |
| 2012/0059332 | A1 | 3/2012 | Woehr et al. |
| 2012/0071819 | A1 | 3/2012 | Bruggemann et al. |
| 2013/0110049 | A1 | 5/2013 | Cronenberg et al. |
| 2013/0296785 | A1 * | 11/2013 | Cabiri ............... A61M 5/3204 604/151 |
| 2014/0194854 | A1 | 7/2014 | Tsals |
| 2016/0228644 | A1 | 8/2016 | Cabiri |

FOREIGN PATENT DOCUMENTS

| | | |
|---|---|---|
| CN | 1756573 A | 4/2006 |
| CN | 1863566 A | 11/2006 |
| CN | 101001661 A | 7/2007 |
| CN | 101687083 A | 3/2010 |
| DE | 1064693 B | 9/1959 |
| FR | 2905273 A1 | 3/2008 |
| JP | 2004-501721 A | 1/2004 |
| JP | 2005-270629 A | 10/2005 |
| JP | 2008-220961 A | 9/2008 |
| JP | 4305704 B2 | 7/2009 |
| WO | 9609083 A1 | 3/1996 |
| WO | 0189607 A2 | 11/2001 |
| WO | 0202165 A2 | 1/2002 |
| WO | 2004069302 | 8/2004 |
| WO | 2005018703 A2 | 3/2005 |
| WO | 2008024810 A2 | 2/2008 |
| WO | 2008076459 A1 | 6/2008 |
| WO | 2010078227 A1 | 7/2010 |
| WO | 2011090955 A1 | 7/2011 |
| WO | 2011104711 A1 | 9/2011 |
| WO | 2011156373 A1 | 12/2011 |
| WO | 2013148435 A1 | 10/2013 |
| WO | 2014159017 | 10/2014 |

* cited by examiner

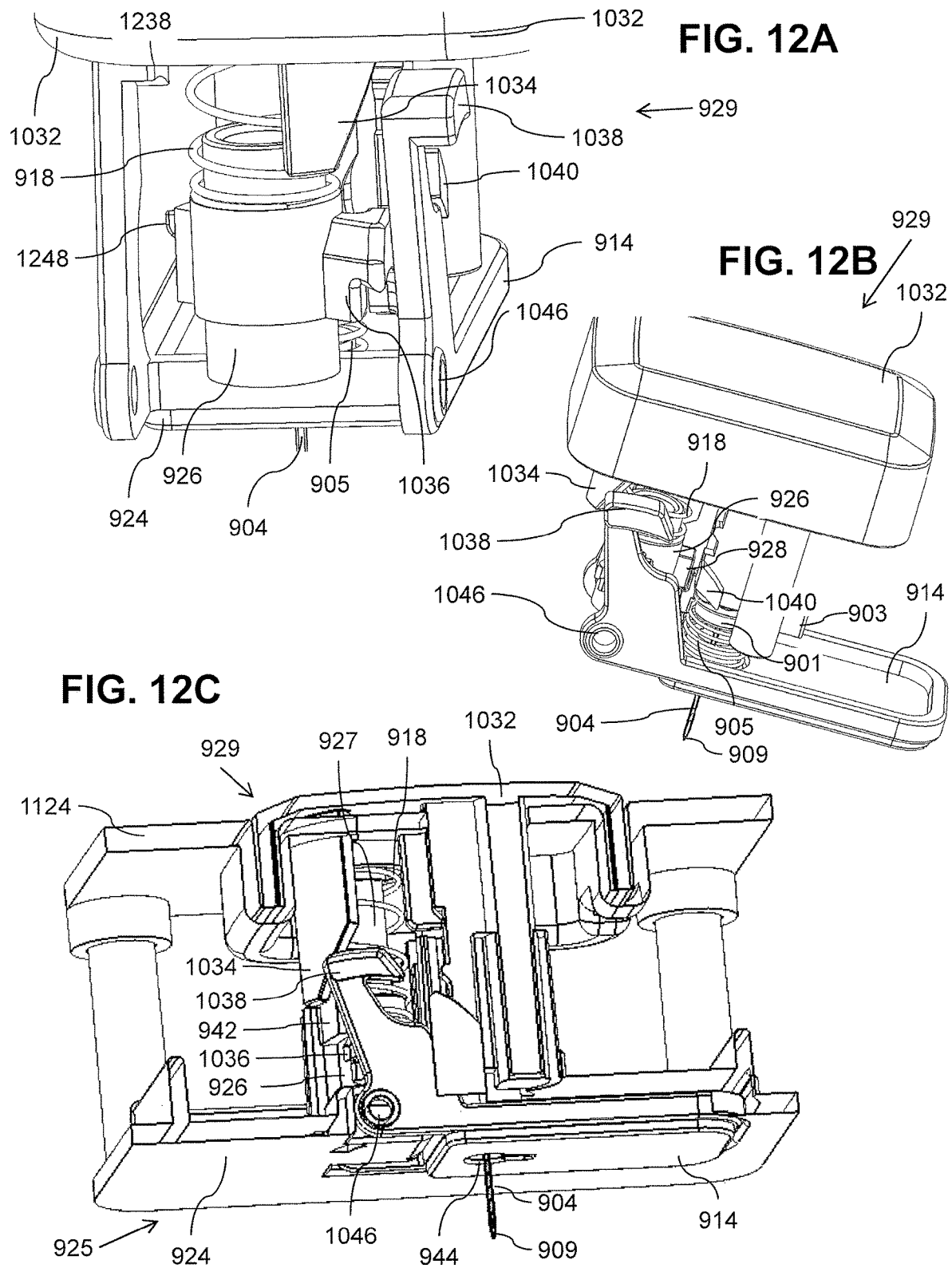

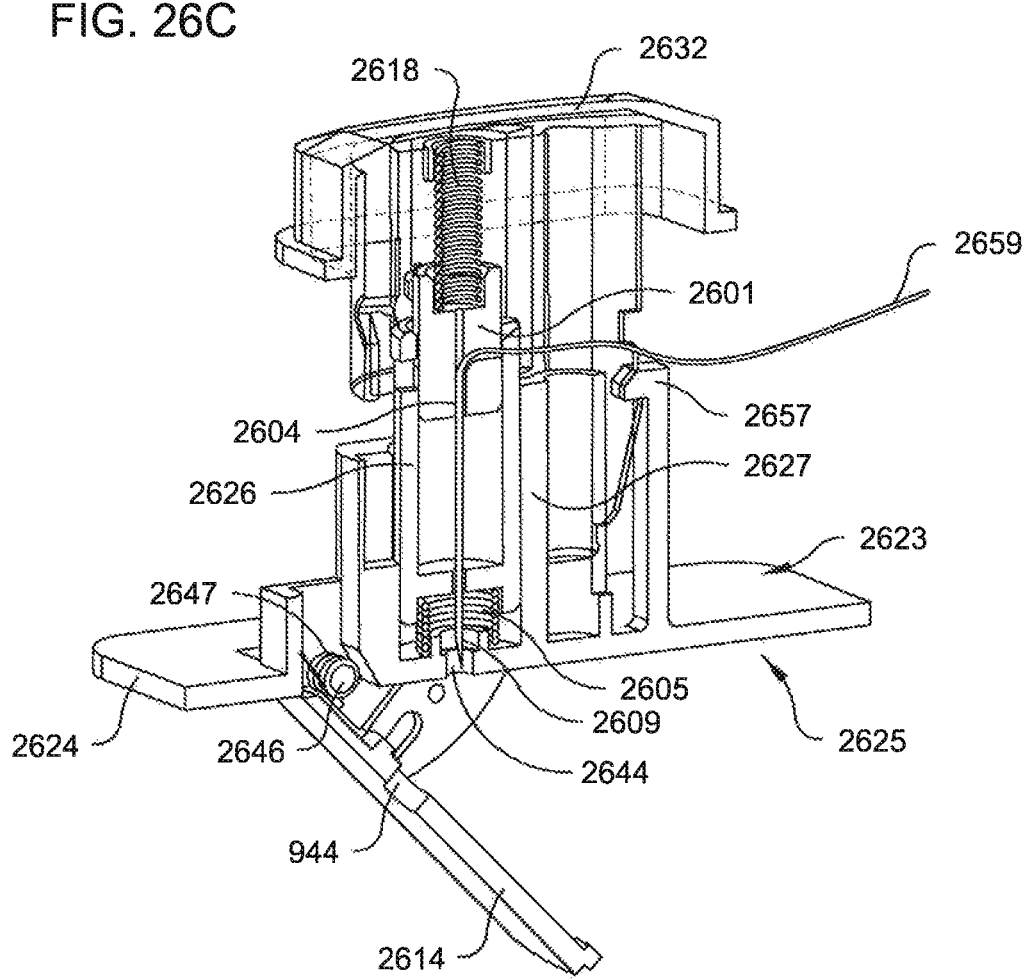

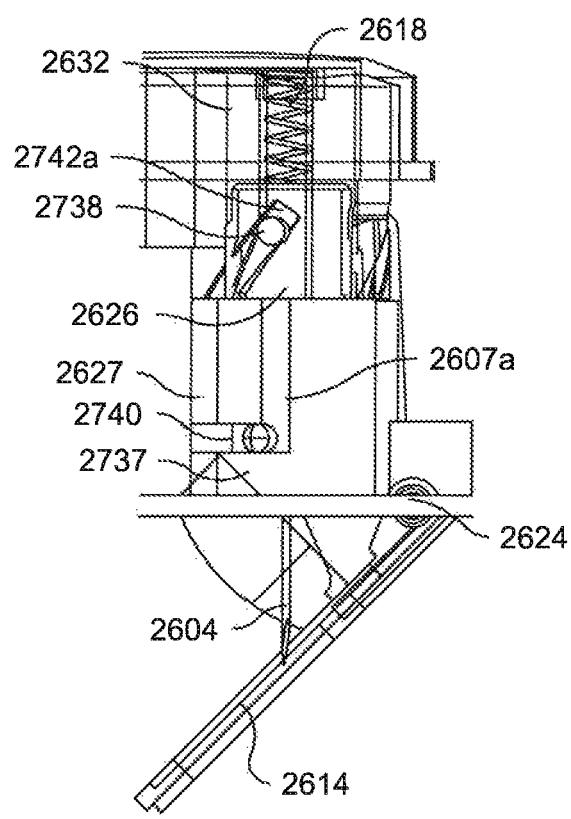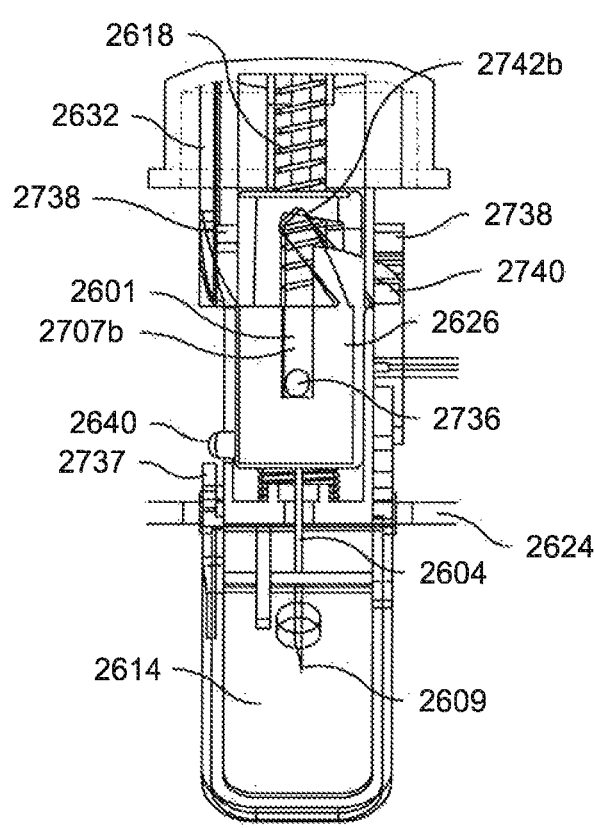
FIG. 29B
FIG. 29C

THREE POSITION NEEDLE RETRACTION

CROSS-REFERENCE TO RELATED APPLICATIONS

This application is a section 371 of International Application No. PCT/US17/35486, filed Jun. 1, 2017, which was published Dec. 7, 2017 under International Publication No. WO 2017/210448 A1, which claims the benefit of U.S. Provisional Application No. 62/344,782, filed Jun. 2, 2016, the disclosures of which are incorporated herein by reference.

RELATED APPLICATION/S

Field and Background of the Invention

The present invention, in some embodiments thereof, relates to a needle extension and/or retraction mechanism and, more particularly, but not exclusively, to a mechanism for protecting a needle tip from stick hazards after removal of an autoinjector for example a patch injector from a subject.

U.S. Pat. No. 8,915,882 relates to "A needle assembly adapted for fluid communication with a vial containing a substance to be delivered to a subject, the needle assembly including a needle held in a needle holder, the needle holder confined to move in a housing, and an activation mechanism for activating delivery of the substance through the needle, the activation mechanism including a safety latch that initially impedes movement of the needle holder, wherein when the safety latch is placed on the subject, the safety latch moves to a position that permits moving the needle holder to cause the needle to protrude outwards of the housing to pierce the subject to allow administration of the substance to the subject."

U.S. Pat. No. 8,152,779 relates to "A needle assembly adapted for fluid communication with a cartridge containing a substance to be delivered to a subject, the needle assembly characterized by a biasing device (70) arranged to apply a biasing force on a needle (28, 116) to cause the needle (28, 116) to protrude outwards of a housing (30, 112) to pierce the subject, and biasing device release apparatus (60) including a biasing device arrester (62) that initially blocks movement of the biasing device (70) and which releases the biasing device (70) when the safety latch (32, 122) moves to a position that permits moving the needle holder (26, 118) to cause the needle (28, 116) to protrude outwards of the housing (30, 112)."

U.S. Pat. No. 7,530,964 relates to a needle device that, "has a needle retraction mechanism that retracts the needle upon removing the device from the skin surface (either intentionally or unintentionally). Once the needle is retracted, the device is rendered inoperative. The needle can be further made inoperative by bending it when one attempts to reuse the device. In another embodiment, a needle opening formed in the base of the housing can be covered to render the needle inoperative when one attempts to reuse the device. In another embodiment, the needle device instead has a needle shield that automatically covers the needle after use."

U.S. Pat. No. 9,072,827 relates to a method and device "for preventing a needle stick hazard in the event of a collapse of a protective needle flap of a portable drug pump. The device may include a needle guide, a secure space and/or a shield. A point of a needle is optionally deflected into a secure space upon collapse of the protective flap. The space may optionally be shielded. Optionally, the support linking the needle to the pump may pivot and/or translate. Optionally, there may be an exposing position wherein the needle protrudes through an opening in the flap. Optionally, the opening may be non-circular."

U.S. Pat. No. 7,530,964 relates to a needle device which, "has a needle retraction mechanism that retracts the needle upon removing the device from the skin surface (either intentionally or unintentionally). Once the needle is retracted, the device is rendered inoperative. The needle can be further made inoperative by bending it when one attempts to reuse the device. In another embodiment, a needle opening formed in the base of the housing can be covered to render the needle inoperative when one attempts to reuse the device. In another embodiment, the needle device instead has a needle shield that automatically covers the needle after use."

SUMMARY OF THE INVENTION

According to an aspect of some embodiments of the invention, there is provided a device for protecting a sharp tip of a hollow needle including: a housing including an inner side and an outer side and an opening between the inner side and the outer side; a needle mount movably connecting the needle to the housing for a movement through the opening between a retracted position wherein the sharp tip is inward of the outer side of the housing and an extended position wherein the sharp tip projects outward from the outer side of the housing; a needle shield, shielding the sharp tip of the needle in the extended position; a lock on the mount inhibiting movement of the needle from the extended position to the retracted position; and a mechanical interlock between the shield and the lock, the interlock releasing the lock to allow retraction of the needle from the extended position to the retracted position when the needle shield is compromised.

According to some embodiments of the invention, the movement of the needle between the extended position and the retracted position is approximately directed along an axis of the needle.

According to some embodiments of the invention, when the needle tip is positioned between the shield and the housing during the shielding.

According to some embodiments of the invention, the compromising includes movement of the shield with respect to the housing during the shielding.

According to some embodiments of the invention, the movement of the needle shield is toward the housing.

According to some embodiments of the invention, the movement of the needle shield is toward the opening.

According to some embodiments of the invention, the compromising includes exerting a force of at least 1 N on the shield.

According to some embodiments of the invention, the force is at least partially directed toward the housing.

According to some embodiments of the invention, the needle shield is pivotally mounted on the housing about a pivot and in the shielding configuration the needle shield is pivoted away from the housing.

According to some embodiments of the invention, the shield is movably mounted on the housing for movement between a primed position and a shielding position and the shield includes a needle opening, and wherein in the primed position, the needle tip is aligned to pass through the needle opening during the movement from the retracted position to the extended position and in the shielding position the needle tip is blocked by a portion of the shield.

According to some embodiments of the invention, the needle shield is movable mounted on the housing between a first position wherein the needle shield is flush with the housing and a shielding position wherein the shield is shielding the sharp tip.

According to some embodiments of the invention, the needle shield is biased toward the shielding position by a biasing device.

According to some embodiments of the invention, the outer side of the housing includes an adhesive skin contact area.

According to some embodiments of the invention, the opening is within the adhesive skin contact area.

According to an aspect of some embodiments of the invention, there is provided a method of safeguarding a needle point of a drug discharge device the device including a housing base including a contact side and an opposite side and an opening between the contact side and the opposite side; the method including: providing the drug discharge device with the contact side of the base contacting an injection surface and the needle point locked in an extended position protruding from the contact side of the device into an injection surface; deploying a needle shield to a deployed position in response to a distancing of the base from the injection surface; wherein in the deployed position wherein the extended position of the needle point is between the base and the needle shield; sensing a compromising of the needle shield after the deploying; and unlocking the needle from the extended position in response to the sensing.

According to some embodiments of the invention, the method further includes: automatically retracting the needle to a retracted position on the opposite side of the base in response to the sensing.

According to some embodiments of the invention, the needle shield is mechanically interlocked with a locking mechanism such that a movement of the needle shield from the deployed position triggers the unlocking.

According to an aspect of some embodiments of the invention, there is provided a method of safeguarding a needle point of a drug discharge device the device including a housing base including a contact side and an opposite side and an opening between the contact side and the opposite side; the method including: providing the drug discharge device with the contact side of the base contacting an injection surface and the needle point in an extended position protruding from the contact side of the device into an injection surface; deploying a needle shield to a deployed position in response to a distancing of the base from the injection surface; wherein in the deployed position wherein the extended position of the needle point is between the base and the needle shield; sensing a compromising of the needle shield after the deploying; and retracting the needle to a retracted position on the opposite side of the base in response to the sensing.

According to an aspect of some embodiments of the invention, there is provided a needle device including: housing base including an opening between an inner side of the base and an outer side of the base opposite the inner side; a needle point mounted for a movement through the opening between a retracted position inward of the inner side of the base and an extended position outward from the outer side of the base; a needle shield having a shielding configuration in which a tip of the needle in the extended position is positioned on the outer side between the base and the needle shield; and a retraction mechanism mechanically interlocked to the needle shield to move the needle from the extended position to the retracted position in response to a compromising of the needle shield.

According to some embodiments of the invention, the outer side of the base includes an adhesive skin contact area.

According to some embodiments of the invention, the compromising includes movement of the shield from the shielded configuration.

According to some embodiments of the invention, the compromising includes exerting a force of at least 1 N on the shield.

According to some embodiments of the invention, the shield has a first position wherein the needle is aligned to pass through the needle opening and a second position wherein the shield is moved with respect to the housing and the needle is blocked by a portion of the shield.

According to some embodiments of the invention, the needle shield is pivotally mounted on the housing about a pivot and in the shielding configuration the needle shield is pivoted away from the housing.

According to some embodiments of the invention, the needle shield is pivotally mounted on the housing about a pivot and in the first position the needle shield is flush with the housing.

According to some embodiments of the invention, the needle shield is biased toward the shielding position by a biasing device.

According to some embodiments of the invention, the movement of the needle shield is toward the base.

According to some embodiments of the invention, the force is at least partially directed toward the base.

According to an aspect of some embodiments of the invention, there is provided a needle device including: housing base including an opening between an inner side of the base and an outer side of the base opposite the inner side, the outer side including a skin contact area; a needle point mounted for a movement through the opening between a retracted position inward of the inner side of the base and an extended position outward from the outer side of the base; a lock mechanism that locks the needle in an intermediate position wherein the needle point is positioned along a path of the movement between 10% to 90% of the distance between the retracted and the extended position.

According to some embodiments of the invention, the needle device further includes: a needle shield movable to a shielding configuration in which a tip of the needle is in the intermediate position and is positioned between the base and the needle shield; and a retraction mechanism mechanically interlocked to the needle shield to move the needle from the extended position to the intermediate position when the needle shield is moved to the shielding position.

According to an aspect of some embodiments of the invention, there is provided a method of safeguarding a hazardous component of a drug delivery device the device including a housing base including an opening between an inner side of the base and an outer side of the base opposite the inner side, the outer side including a skin contact area; the method including: supplying the device with the hazardous component in a first retracted position; extending the hazardous component in response to an external trigger from the first retracted position to an extended position protruding outward from the outer side of the base; locking the hazardous component in the extended position; delivering the drug with the hazardous component in the extended position; retracting the hazardous component from the extended position to a second retracted position at least 1 mm distant from the first retracted position; holding the hazardous component in the second retracted position.

According to some embodiments of the invention, the hazardous component includes a sharp tip of a needle the method further including shielding the sharp tip by a housing of the device in at least one of the first retracted position and the second retracted position.

According to some embodiments of the invention, the hazardous component includes a sharp tip of a hollow needle and wherein the delivering is through a channel of the hollow needle.

According to some embodiments of the invention, the holding is for at least 1 second.

According to some embodiments of the invention, the holding indefinitely.

According to some embodiments of the invention, the method further includes: releasing the holding in response to an external stimulus.

According to some embodiments of the invention, the external stimulus includes a compromising of a needle shield.

According to some embodiments of the invention, the retracting is in response to an end of the delivering.

According to some embodiments of the invention, the retracting is in response to an external stimulus.

According to some embodiments of the invention, the external stimulus includes a distancing of the delivery device from a skin of a user.

According to some embodiments of the invention, the second retracted position is on the outer side of the base and the first retracted position is on the inner side of the base.

According to some embodiments of the invention, the method further includes: retracting the hazardous component from the second retracted position to a third position on the inner side of the base.

According to some embodiments of the invention, the third position is substantially the same as the first position.

According to some embodiments of the invention, the further retracting is in response to an external stimulus.

According to some embodiments of the invention, the external stimulus includes compromise a shield of the hazardous component.

According to some embodiments of the invention, the method further includes: deploying a shield after the delivering to shield the hazardous component in the second retracted position.

According to some embodiments of the invention, the further retracting occurs automatically after a time delay after the retracting.

According to some embodiments of the invention, the second retracted position is intermediate between 10% to 90% along a path of motion between the extended position and the first retracted position.

According to some embodiments of the invention, the first retracted position is intermediate between 10% to 90% along a path of motion between the extended position and the second retracted position.

According to some embodiments of the invention, the method further includes: providing a retraction mechanism for the retracting and a sensor, the sensor mechanically interconnected to the retraction mechanism; moving the sensor in response to a distancing of the delivery device from the skin of a user; triggering automatically the retracting by the moving.

According to some embodiments of the invention, in the extended position the hazardous component protrudes outside the housing through an opening at least 2 mm from the opening and in the intermediate position the hazardous component protrudes outside the housing through an opening no more than 1 mm.

According to some embodiments of the invention, the method further includes: deploying a shield while the hazardous component is in the second retracted position such that the hazardous component is located between the shield and a surface of the outer side of the base.

According to some embodiments of the invention, the deploying is triggered by the moving of the sensor.

According to some embodiments of the invention, the holding includes blocking movement of the hazardous component from the second retracted position by a mechanical interconnecting between the sensor and the retraction mechanism.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 12A-12D are a perspective cutaway and cross sectional illustrations of a needle mechanism in an active state in accordance with an embodiment of the current invention;

FIG. 26C is a cutaway view of a needle mechanism in accordance with an embodiment of the current invention;

FIGS. 29A-29C illustrate a needle retraction mechanism in a partially protected state in accordance with an embodiment of the current invention and FIGS. 30A-30C illustrate a needle retraction mechanism in a fully protected state in accordance with an embodiment of the current invention.

DESCRIPTION OF SPECIFIC EMBODIMENTS OF THE INVENTION

Figure 1:
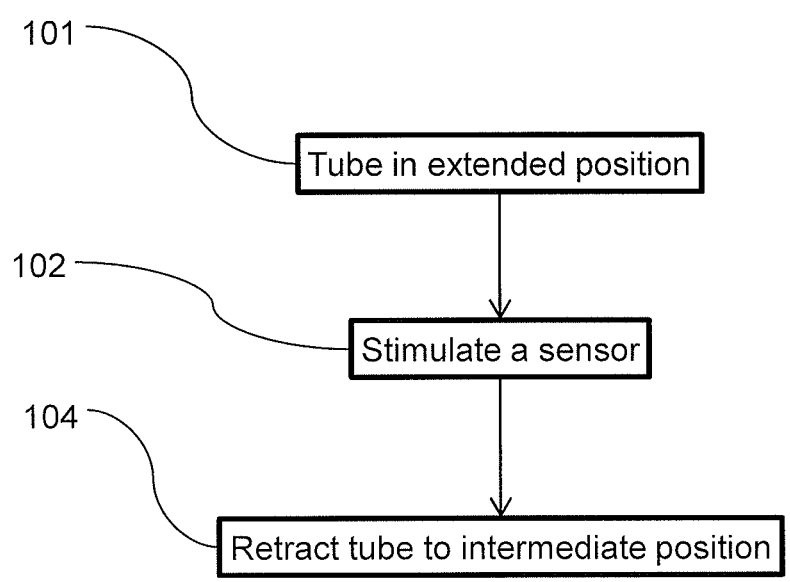
FIG. 1 is a flow chart illustration of a method of partially retracting a needle in accordance with an embodiment of the current invention.

The present invention, in some embodiments thereof, relates to a needle extension and/or retraction mechanism and, more particularly, but not exclusively, to a mechanism for protecting a needle tip from stick hazards after removal of an autoinjector for example a patch injector from a subject.

Overview

An aspect of some embodiments of the present invention relates to an autoinjector with a needle that automatically partially retracts when the injector is removed from the skin of a subject. In some embodiments, an injector needle extends to an active position with an exposed portion of the needle extending outward from a skin contact surface and/or from an opening of a base of a housing of the injector. Optionally, in the partially retracted state a smaller portion of the needle extends outward from the skin contact surface and/or the opening. Optionally the smaller portion of the needle is covered by a shield for example to avoid a stick hazard.

In some embodiments a sensor may be stimulated by an external event, for example, a sensor registers when the injector is placed onto and/or distanced from the skin of a subject. Optionally, sensor output triggers needle retraction and/or unlocks the needle from the extended position. For example, the sensor may include a mechanical component in contact with the skin and/or mechanically interconnected to a needle retraction mechanism and/or a needle locking mechanism. For example, the mechanical connection may lock the needle in the extended position when the sensor is against the skin. Distancing a portion of the injector from the skin optionally releases the mechanical interconnection to unlock the needle and/or to trigger partial retraction of the needle.

In some embodiments, reexposure of a needle is inhibited. For example, after retraction, a locking mechanism may prevent the needle from being reextended. Alternatively or additionally, a shield may be deployed blocking the needle. Optionally the shield may be locked in place preventing reexposure of the needle. Alternatively or additionally, further excitation of the sensor (for example moving the sensor) may cause and/or allow further retraction of the needle to a protected location. Alternatively or additionally, a needle may retract, lock and/or unlock in connection to an event and/or status of the injector, for example, when all of a payload has been discharged and/or when there is an occlusion in the system and/or in response to a user action and/or after a time lapse.

In some embodiments a device may include a needle retraction mechanism and/or a needle shield. For example, the skin sensor may be designed to shield the needle and/or prevent a stick hazard. Optionally the shield may be deployed when delivery finishes and/or when the device is distanced from an injection surface (e.g. the skin of a user). Optionally or additionally, the shield may protect the needle when the needle is in an intermediate position. For example the shield and/or sensor may have the form of a flap covering the needle point and/or a sleeve surrounding the needle point.

In some embodiments a needle may be held in a partially retracted position for a time period. For example, the needle may be held in the partially retracted position for between 0.1 sec to 1 sec and/or between 1 sec to 5 sec and/or between 5 sec. to 20 sec and/or longer. Alternatively or additionally, the needle may be held until an external stimulus causes it to be released. For example the external stimulus may include a force exerted on an element of the drug delivery device. For example the needle may be released in response to a force on a needle shield and/or a force on the needle and/or a movement of the needle shield.

In some embodiments, a needle may be retracted from an extended position to an intermediate position and/or a fully retracted position in response to an external stimulus. For example, the needle may be retracted in response to the delivery device being distanced from an injection surface (for example the skin of a subject). For example the needle may be retracted in response to removal of a skin contact surface of the device from the injection surface. For example the needle may be retracted in response to an action of a user, for example pushing a retraction button. Alternatively or additionally the needle may be removed in response to a status of the delivery device. For example, the needle may be retracted when the device completes delivery of a prescribed dose and/or upon a malfunction of the device.

An aspect of some embodiments of the present invention relates to a multi-level safety mechanism to protect a needle. In some embodiments, the safety mechanism includes a first component that protects the needle and a second component that is activated in response to changes in the first component. For example, a needle shield in a deployed configuration may block a sharp tip of the needle. When the needle shield is compromised, for example, a force is applied to the shield and/or the shield moves from the deployed configuration, the needle is optionally neutralized. For example the needle may be retracted and/or folded and/or moved to a protected position.

In some embodiments a mount connecting a needle to a drug delivery device may include a needle retraction system and/or multiple protection measures and/or a redundant needle protection system. Optionally, the needle mount may allow movement of the needle with respect to the housing. For example, the housing may include a skin contact surface and/or a needle opening in the skin contact surface. Optionally, the needle is mounted to the housing to allow movement of needle in a longitudinal directional and/or movements that are nearly longitudinal (for example around a pivot approximately perpendicular to and/or far from the needle [for example the distance to the fulcrum may be more than 4 times the length of the needle]). Optionally, a point of the needle moves from a location inside the housing to a location outside the housing. For example, the needle point may pass through the needle opening. Optionally the housing may include a skin contact surface. In some embodiments, the needle opening may pass through the skin contact surface. Optionally the skin contact surface includes an adhesive for attachment to an injection site on a subject. In some embodiments, the needle is hollow. For example, an end of the needle opposite the tip may be connected to a drug reservoir. For example, the needle may be extended into the skin of a subject and/or the needle may act as a fluid path for injecting the drug from the reservoir into the subject.

In some embodiments, an interconnection between a needle shield and a retraction mechanism may lock the needle in the extended and/or partially retracted position. For example, the needle may be locked in the extended and/or partially retracted position while the needle shield is deployed. Movement of the needle shield may release the lock and allow the needle to be further retracted. In some embodiments, the needle may retract automatically. Alternatively or additionally, the needle may be unlocked and/or retract in response to an external force. For example, the needle shield may be interlocked with the needle retraction mechanism such that a force on the needle shield is translated to a force pulling back the needle to a retracted and/or protected position. Alternatively or additionally, the needle shield may have a natural path of movement, for example a path of least resistance to movement that intersects the needle. Movement of the shield along the path optionally causes the shield to contact the needle. Contact between the shield and the needle optionally neutralizes the needle, for example by bending the needle and/or pushing it into a protected position.

An aspect of some embodiments of the current invention relates to a needle having 3 or more stable positions. For example, a needle may have a retracted position, an extended position and/or third position. For example, the third position may include a partially retracted position and/or an intermediate position between the extended and retracted positions. Optionally, in the partially retracted position the needle may be entirely retracted into a housing of the device. Alternatively or additionally, in the partially retracted position, a portion of the needle may extend out of the housing. For example the portion of the needle extending out of the housing in the partially retracted position may be shorter than the portion extending out in the extended position.

In some embodiments, a needle retraction mechanism may be locked and/or unlocked and/or triggered by a skin sensor. Optionally, the skin sensor may be mechanically interlocked with the needle retraction mechanism. For example, when the sensor detects removal from the skin, the needle may be unlocked from an extended position. Alternatively or additionally, when the sensor detects removal from the skin, the needle may be automatically retracted to a partially and/or fully retracted position. For example, when the sensor detects removal from the skin the needle retraction mechanism may be moved to and/or locked to a partially and/or fully retracted position. Alternatively or additionally, other events may lock, unlock and/or automatically move the needle retraction mechanism between positions.

In some embodiments, in an active state, a sharp needle and/or cannula may extend out of the device. In a safeguarded state, the needle is optionally partially retracted. For example, in the extended state a portion of the needle may be exposed and/or extend outside a housing of the device. Optionally, in the partially retracted state, a smaller portion of the needle may be exposed and or extend out of the device than in the extended state. For example, in the extended state a needle tip may extend a distance away from a housing of the device. Optionally, in the partially retracted state, the needle may extend away from the device less than in the exposed state. Optionally, the device may have a fully retracted state and an intermediate state. In the intermediate state the needle may be on a path between the fully retracted state and the extended state. For example, during injection a needle may extend a distance ranging for example between 2 to 5 mm and/or 5 to 8 mm and/or 8 to 12 mm out of the skin contact surface. In the partially retracted state a needle may extend a distance ranging between 20 to 70% and/or 70 to 85% and/or 85 to 95% of the fully extended distance. Optionally, in the partially retracted state the point of the needle may be located ranging for example between 0.5 to 1 mm and/or 1 mm to 3 mm and/or 3 mm to 5 mm and/or 5 to 10 mm outward from the position in the fully retracted state. Needle gauge may range for example between 34 to 30 G and/or 30 G to 26 G and/or 26 to 22 G. The needle retraction stroke is optionally at least 1 mm longer than needle extended length. Optionally the needle may be extended by a spring driven mechanism. For example the force exerted by the spring at the needle may range between 20 to 40 gr (grams force) and between 40 to 80 gr and/or greater than 80 gr.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the figures, FIG. 1 is a flow chart illustration of a method of partially protecting a hazardous element in accordance with an embodiment of the current invention. In some embodiments, a hazardous element includes a sharp hazard and/or a biohazard and/or burn hazard and/or a toxic hazard and/or a chemical hazard (e.g. corrosive). For example a tip of a tube and or a needle may include a sharp hazard. The tube is optionally locked 101 in an extended position. A sensor is optionally mechanically interconnected with a locking mechanism. Stimulating 102 the sensor optionally causes releasing of the lock allowing the needle to be retracted 104 from the extended position to an intermediate position.

In some embodiments a tube (for example a needle and/or a cannula) may be used for discharging a drug into a patient. The tube may be locked 101 in an extended position, for example during discharge.

In some embodiments, drug discharge device will include a sensor. For example a sensor may be stimulated 102 when a device is removed from a patient. For example, a mechanical sensor may be biased to move outward. Outward movement of the sensor may be blocked when the device is on an injection surface, for example on the skin of the subject. When the device is removed from the surface, the sensor may be released and/or move. Alternatively or additionally a sensor sense light and/or may sense heat and/or conductivity of the surface. When the sensor is stimulated 102 for example detecting that the device was removed from the surface, the detector may unlock the tube allowing it to retract 104 from the extended state. Alternatively or additionally, when the sensor detects 102 that the device was removed from the surface, the sensor may trigger retraction of the tube. Alternatively or additionally, when the, when sensor detects that the device was removed from the surface, it may lock a needle retraction mechanism inhibiting the needle from moving to some position. For example, the needle may be inhibited from reaching a fully retracted position. For example the needle may be inhibited from returning to the extended position. Alternatively or additionally, a sensor may include a sensor of a state of the injection device, for example finishing of discharge and/or a malfunction.

Figure 2:
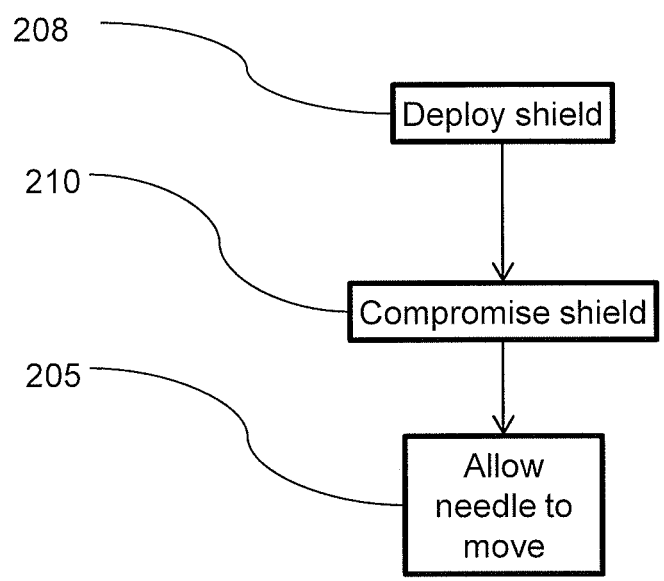
FIG. 2 is a flow chart illustration of a method of shielding and retracting a needle in accordance with an embodiment of the current invention.

FIG. 2 is a flow chart illustration of a method of neutralizing a hazard in accordance with an embodiment of the current invention. For example, the hazard may be a stick hazard from a needle point. For example, a system may include a safety backup in case a first neutralizing mechanism is compromised. In some embodiments a needle may be neutralized by shielding 208 the needle. Optionally, the needle may be moved 205 for example to a protected position when the functioning of the shield is compromised 210, for example by tampering with the shield. For example, compromising a shield may include applying a force to a shield. For example the force may be directed in a failure direction (for example a collapse direction and/or an opening direction). The force may range for example between 10 gr to 100 gr and/or 100 gr to 1000 gr and/or 1000 gr to 5000 gr and/or 5000 gr to 10000 gr. Compromising a shield may include, for example, moving a shield with respect to a hazard and/or a housing. For example, movement of the shield may include, at the point on the shied of maximum movement, movement of between 0.1 mm and 1 mm and/or between 1 mm and 5 mm and/or between 5 mm and 2 cm and/or more than 2 cm.

In some embodiments, allowing the needle to move 205 may include retracting the needle to a protected location. Alternatively or additionally, the needle may be allowed to move and/or fold, for example by unlocking a retraction mechanism and/or a needle holder. For example, once the shield is unlocked, if the shield fails, for example collapses, the shield may cause the needle to collapse and/or be neutralized.

In some embodiments, compromising 210 the shield may include applying a force to the shield. For example when a force is applied pushing the shield towards a collapsed state and/or pulling a shield away from the shielding position, movement 205 of the needle may be triggered. For example when a force is applied to the shield by an object pushing itself between the shield and the needle, movement 205 of the needle may be triggered.

In some embodiments, a shield may be deployed 208 while a needle in an extended position. Optionally a needle may be locked into an extended position while discharging a drug into a subject. For example, after discharge and/or after removal of the discharge device from the subject, a shield may be deployed 208 while the needle remains in the extended position. Alternatively or additionally, shield may be deployed 208 while a needle is in an intermediate position. For example, at the end of discharge and/or when the device is removed, a needle may be partially retracted and/or the shield may be deployed to protect the needle in the partially retracted position.

Figure 3:
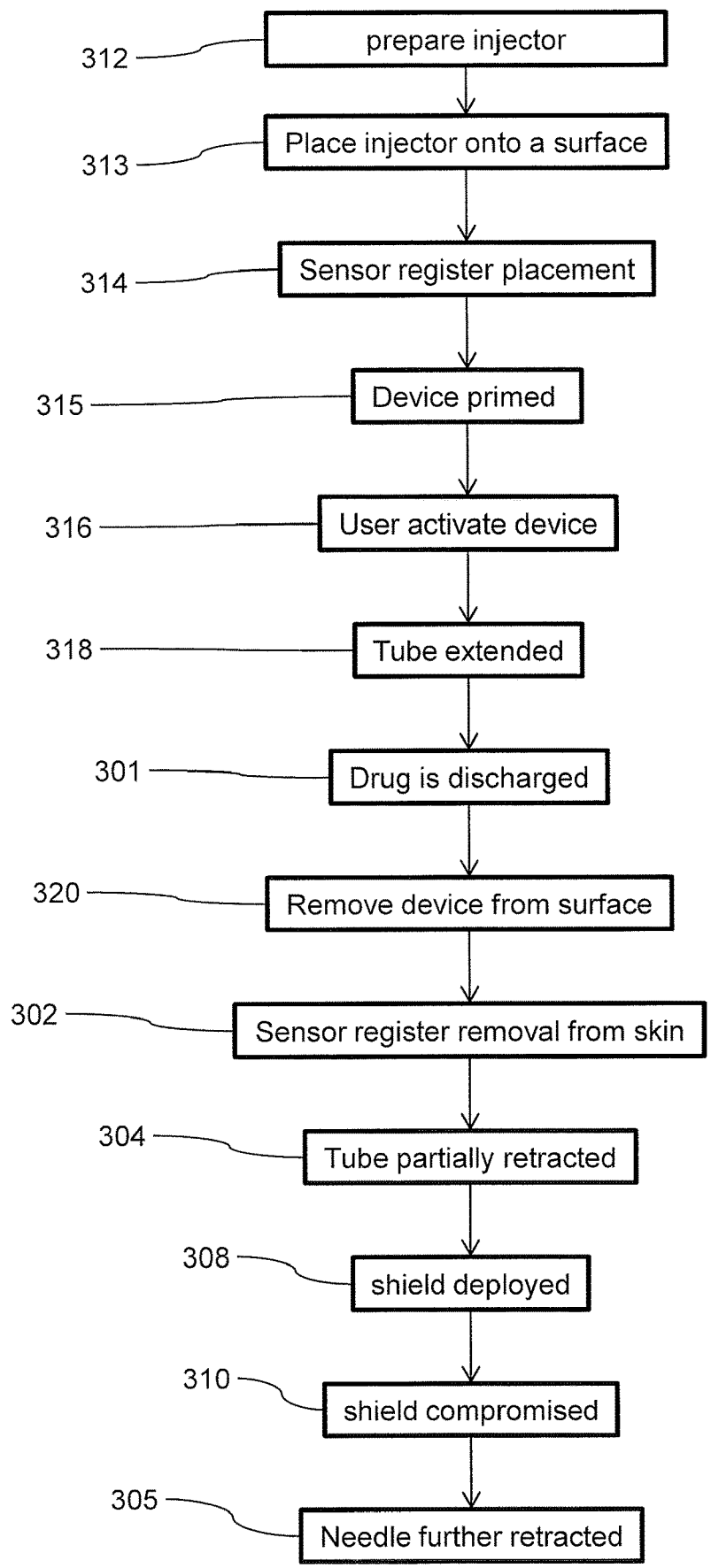
FIG. 3 is a flow chart illustration of a method of using and retracting a needle in accordance with an embodiment of the current invention.

FIG. 3 is a flow chart illustration of a method of using and/or retracting a tube in accordance with an embodiment of the current invention. In some embodiments, a device may include an automatic tube insertion and/or stick hazard protection system. Optionally, the device may have multiple stages of extension and retraction. For example, an extension mechanism may insert the tube (for example a hypodermic needle) into a subject. For example, a shield may cover the needle and/or ameliorate a stick hazard. For example, a retraction mechanism may move a needle to a fully and/or partially protected position. The shielding and/or retracting are optionally integrated. Optionally, deployment and/or withdrawal of a shield may be triggered by a sensor and/or by a state of the device and/or by a user action. Optionally, extension and/or retraction of a needle may be triggered by a sensor and/or a state of the device and/or a user action. For example, integrated movements of the shield and/or needle may facilitate needle insertion, drug discharges and/or protection against a stick hazard. In some embodiments, a single component may serve multiple functions. For example a sensor may also shield a needle and/or a retraction mechanism may also serve as a sensor. Note that FIG. 3 illustrates a large number of actions. Some actions of the method may be performed independently of others. Some of the actions may be performed in the absence of others.

In some embodiments, an injector may be prepared 312 for use. For example, preparing 312 an injector for use may include deploying a skin sensor. Optionally an injector is supplied to a user in a stored state. For example, unwrapping the device (for example removing it from a blister package, removing a protective adhesive covering and/or removing a battery isolator) may prepare 312 the device for use. For example, removing the device from a blister package may uncover a sensor and/or activate a mechanical sensor. For example a mechanical skin sensor may be freed to deploy from the base of the device as the device is lifted from a blister package and/or when an adhesive cover is removed from the base.

In some embodiments, an injector may be placed 312 onto an injection surface, for example the skin of a subject. Optionally, a sensor may register 314 placement 313 of the device. For example, a mechanical sensor may register contact with the surface. Alternatively or additionally, the sensor may be operative to register a quality of the placement 313 of the device. For example, a sensor may register 314 the temperature and/or conductivity of the surface and/or a sensor may register 314 the distance from a point on the injection surface to a point on the injector and/or whether a position of the injector with respect to the surface is stable and/or changes. For example, if the distance between the sensor location and the injector surface is not stable, the device may alert the user that the device is improperly placed. Exemplary sensors that might be used and/or have potential to detect proper placement on the skin include for example: capacitance, magnetic and/or optic. Optionally, based on output of one or more sensors, a controller may confirm that a needle shield is closed and/or that the device has established contact with skin.

In some embodiments, a device may be primed 315 before use. For example, priming may be performed automatically when the proper placement 313 of the device is registered. For example, a mechanical sensor may be interconnected with a needle extension mechanism. For example, placement 313 of the device on the skin of a subject may cause movement of the sensor and/or movement of the sensor may unlock the needle extension mechanism. Optionally the priming of the system, for example unlocking of the needle extension mechanism, occurs automatically in response to registering 314 of the sensor. Alternatively or additionally, the priming of the system may require a user action (for example pushing an OK button once the device has been properly placed 313).

In some embodiments, a device may be activated 316 by a user action. For example, once the device has been placed 313 and/or primed 315, a user may press a button to trigger needle extension 318. Optionally the needle extends out of the base of the device and/or into the skin of the subject. In some embodiments, a needle may be hollow and/or a drug may be injected through the needle. Alternatively or additionally, after insertion a needle may be removed leaving behind a tube (for example a cannula) for discharge 301 of a drug. Alternatively or addition, movement of the sensor may automatically trigger activation of the device and/or needle extension 318. Alternatively or additionally, a user may manually extend 318 the needle (for example the user may push against a surface which drives the needle into his skin). Optionally, a drug may be discharged 301 through the needle into the subject.

In some embodiments, a user may remove 320 a device from a surface. For example after discharge 301 of the drug, a user may remove 320 the device from his skin. Alternatively or additionally, a user may remove 320 the device before discharge has completed (e.g. prematurely). Alternatively or additionally, a user may remove 320 the device when a malfunction occurs. Optionally a sensor may register 302 removal of the device.

In some embodiments, in response to registering 302 removal of the device from the skin, the device may be safeguarded. Alternatively or additionally the device may be safeguarded in response to a completion of discharging and/or a malfunction. Optionally, safeguarding the device includes neutralizing a stick hazard. For example, a delivery tube (e.g. a needle) may be partially retracted 304 and/or a shield may be deployed 308. For example, in the deployed state, the shield may cover the tip of the needle. For example the shield may deploy 308 to cover the tip of the needle while the needle is in the partially retracted 304 state. In some embodiments, a skin sensor may include a needle shield.

In some embodiments, a safeguard mechanism may include a redundant and/or failsafe protection mechanism. For example, a needle may include a further retraction 305 mechanism that moves the needle to a protected location when there the device detects a possible compromising 310 of the needle shield.

Figure 4:
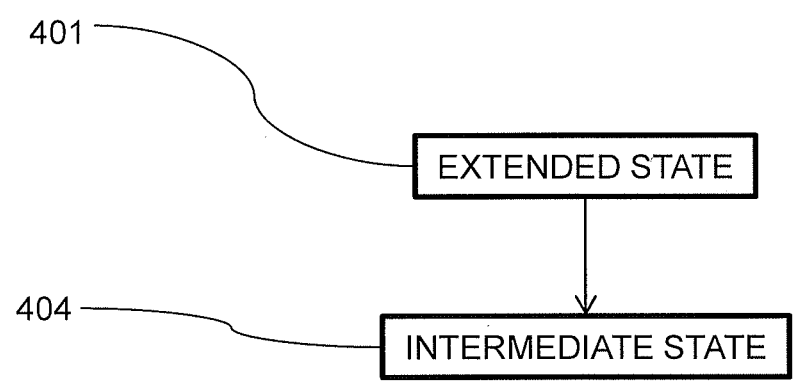
FIG. 4 is a state diagram illustration of a partially retractable needle in accordance with an embodiment of the current invention.

FIG. 4 is a state diagram illustration of a retractable needle in accordance with an embodiment of the current invention. In some embodiments a drug discharge device may have an active state in which an access tube (for example a hypodermic needle) extends out of the device. Optionally, the device may also have a safeguarded state in which the tube is partially retracted. For example, when discharge of the drug is interrupted in the active state, the device may automatically switch to the safeguarded state.

In some embodiments, in active state 401, a sharp needle and/or cannula may extend out of the device. In a safeguarded state the needle is optionally partially retracted 404. For example, in the extended state a portion of the needle may be exposed and/or extend outside a housing of the device. Optionally, in the partially retracted state, a smaller portion of the needle may be exposed and or extend out of the device than in the exposed state. For example, in the extended state a needle tip may extend a distance away from a housing of the device (for example the distance from the device may be operationally defined as the shortest distance between the needle point and any point on the device and/or as the distance between the needle point and a particular location for example a sensor location on the device). Optionally, in the partially retracted state, the needle may extend away from the device less far than in the exposed state. Optionally the device may have a fully retracted state and/or an intermediate state. In the partially retracted state the needle may be on a path between the fully retracted state and the extended state. In some embodiments, a shield may cover a tip of the tube in the partially contracted state.

Figure 5:
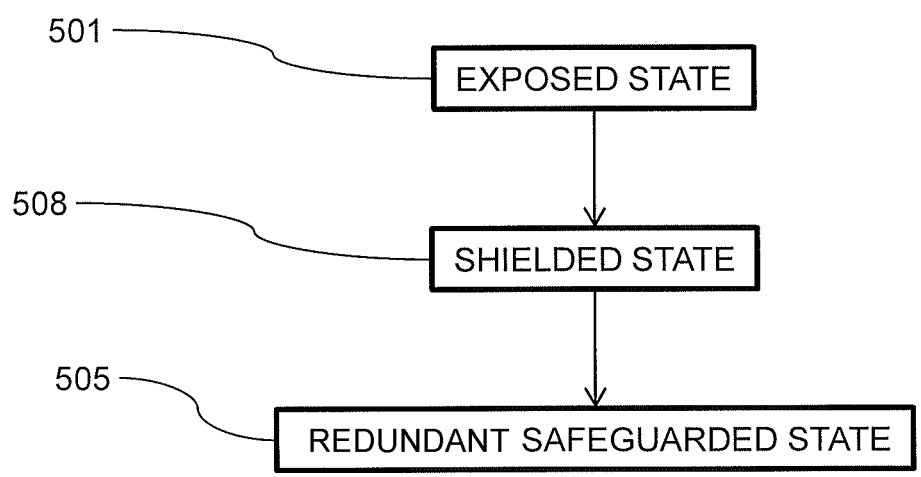
FIG. 5 is a state diagram illustration of a needle in accordance with an embodiment of the current invention.

FIG. 5 is a state diagram illustration of a needle in accordance with an embodiment of the current invention. In some embodiments, an injector may have an exposed state 501 and/or multiple safeguarded states. For example, in a first safeguarded shielded state 508, a sharp point of a tube may be covered by shield protecting a user from a hazard. The device may have a second safeguarded state 505. For example the device may revert to the second safeguarded state when there is a sign of compromise of protection of the first safeguarded state. For example in the second safeguarded state 505 the tube may be retracted to a safe location. For example, when a force is applied to the shield, the tube may be retracted into the second safeguarded state.

Figure 6:
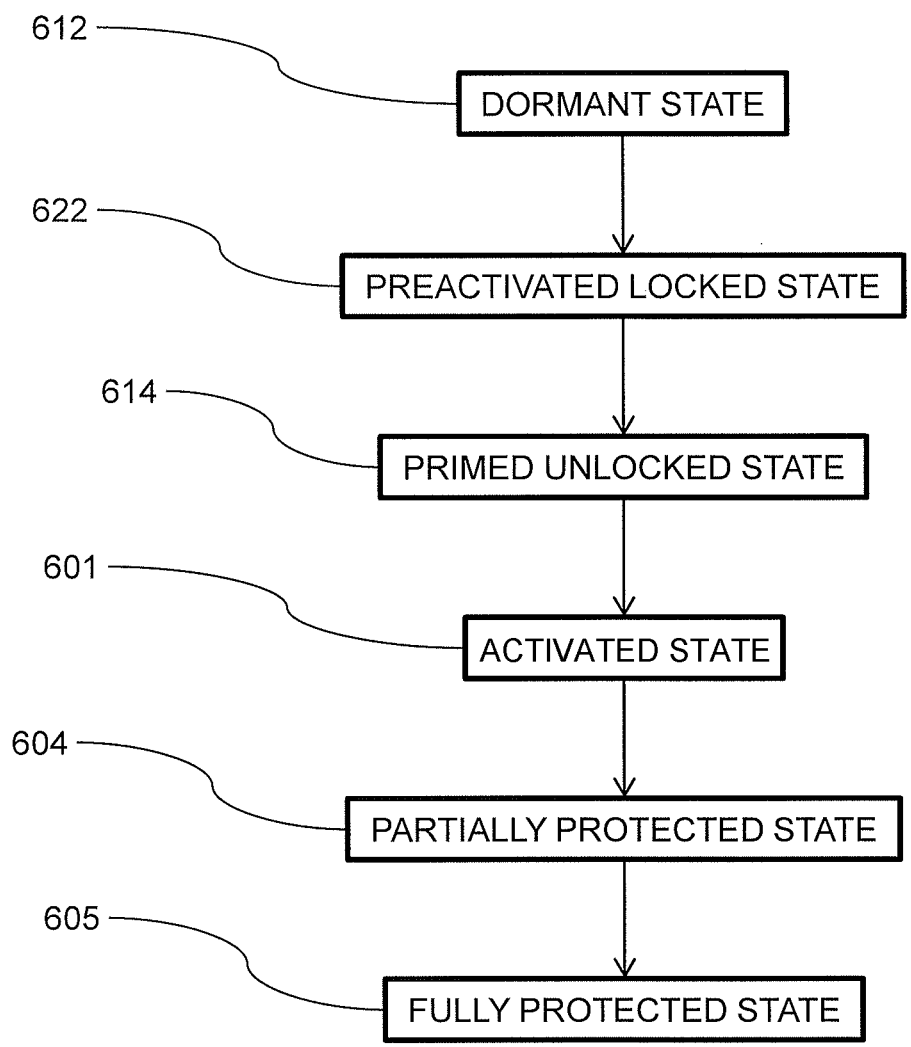
FIG. 6 is a state diagram illustration of a multi-position needle in accordance with an embodiment of the current invention.

FIG. 6 is a state diagram illustration of a multi position needle in accordance with an embodiment of the current invention.

In some embodiments an injector may have a dormant 612 state. For example, in dormant state 612 an energy storage device (for example a battery) may be isolated, for example avoiding draining energy. Optionally in the dormant state 612, a component of the system is positioned to be protected against damage during storage and/or transport. Optionally in the dormant state a hazardous component (for example a needle tip) is locked in a protected position and/or a shield is locked around the hazardous component.

In some embodiments, the device includes a preactivated state 622. For example the device may enter the preactivated state 622 from a dormant state 612. For example, the switch to the preactive state may be caused by an action of a user and/or a supplier. For example, the device may enter the preactivated state 622 when the device is removed from a package and/or in response to a user and/or a helper and/or a supplier and/or a medical aid switching the device on. Optionally, in the preactivated state 622 a hazardous component is locked and/or shielded. Optionally in the preactivated state 622 a sensor is initiated.

In some embodiments a device includes a primed state 614. For example, a device may switch from a preactivated state 622 to a primed state 614 when a sensor registers that the device is ready for use (for example it has been placed on the skin of a subject). Optionally in primed state 614 a hazardous component is unlocked and/or ready for exposure. For example, when a preactivated device is placed on the skin of a user, a skin sensor may register placement on the skin and/or unlock a needle. Alternatively or additionally, a device may not have separate preactivated 622 and primed 614 states. For example, the device may be preactivated and/or primed simultaneously.

In some embodiments, a device may include an activated state 601. For example, a user may activate a primed device, for example by pressing an activation button. In the active state 601 a hazardous component may be exposed. For example, a needle may be extended out of a housing of the device. For example in the activated state 601 a drug may be discharged through a tube (e.g. an extended hypodermic needle) into a subject.

In some embodiments a device may include a partially protected state 604. For example at the completion of drug discharge and/or upon a malfunction and/or upon removal of the device from the skin a hazardous component may be partially protected. For example a needle may be shielded and/or partially retracted. The partially protected position is optionally stable. For example, the device may remain in the partially protected state 604 until disturbed.

In some embodiment a device may include a fully protected state 605. For example, if there is some compromise of the protection of the hazardous component in the partially protected state 604, the device may revert to a fully protected state 605. For example, if a force is applied to a needle shield protecting a needle in a partially protected state 604, the needle may retract to a fully protected state 605. Optionally a device may be permanently locked and/or disabled in one or both of the partially protected state 604 and/or the fully protected state 604.

Figure 7:
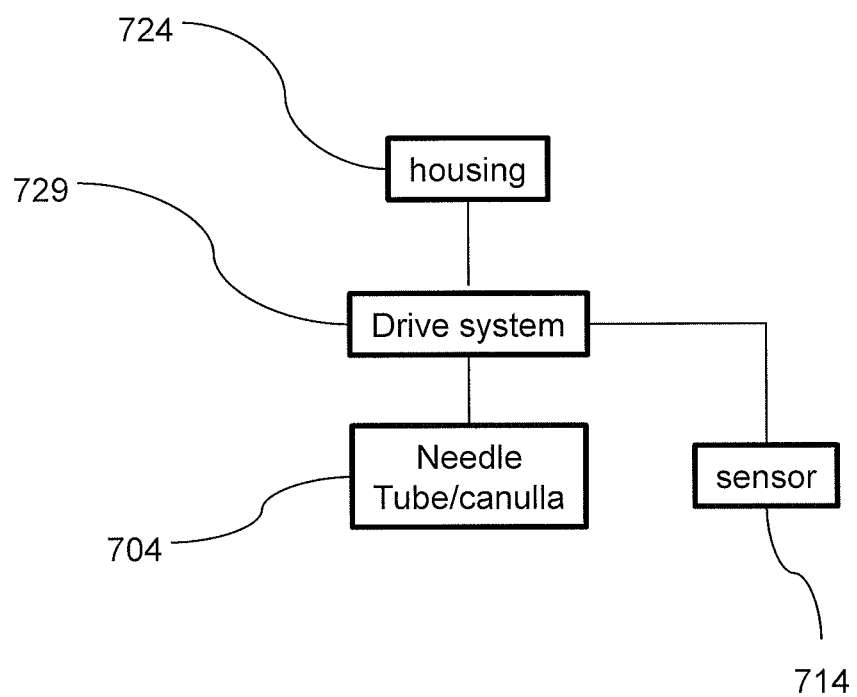
FIG. 7 is a block diagram illustration of a partially retractable needle in accordance with an embodiment of the current invention.

FIG. 7 is a block diagram illustration of a drug delivery system in accordance with an embodiment of the current invention. Optionally, a device may include a drive system 729. Optionally, drive system 729 may expose and/or protect a hazardous component. For example a hazardous component may include a sharp needle 704. For example drive system 729 may expose a sharp needle by extending it out of a housing 724. For example a drive system 729 may protect a sharp needle 704 by retracting it back into housing 724. In some embodiments there may be an intermediate state between a fully retraction and extension (for example a partially retracted state). For example drive system 729 may move a hazardous component to an intermediate position and hold it there. Optionally, drive system 729 is responsive to a sensor 714. For example, drive system 729 may be connected to sensor 714 by means of an electromechanical and/or a mechanical connection and/or through a logical component (for example a processor). In some embodiments, a drive system and/or a sensor may include an electro magnet, and/or a linear actuator and/or a piezoelectric element.

Figure 8:
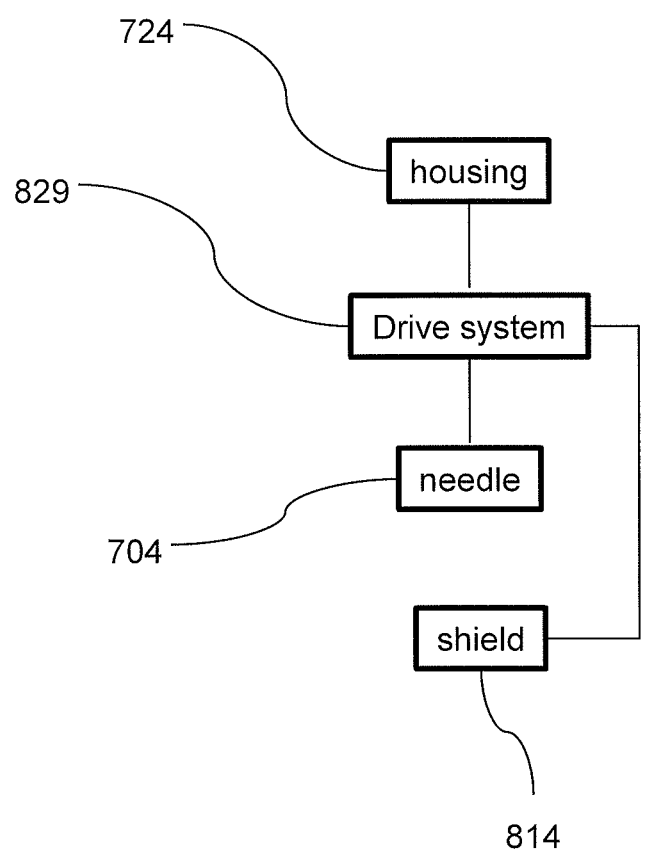
FIG. 8 is a block diagram illustration of a needle mechanism in accordance with an embodiment of the current invention.

FIG. 8 is a block diagram illustration of a protection mechanism in accordance with an embodiment of the current invention. Optionally a protection mechanism may include a shield 814. For example, in some configurations shield 814 may cover and/or protect a hazardous element (e.g. a needle 704). Optionally shield 814 may be synchronized with a drive system 829. For example, needle 704 may be protected by shield 814 when shield 814 is in a deployed position and needle 704 is in a retracted position and/or an intermediate position. For example, needle 704 may retract when shield 814 deploys. For example, needle 704 may partially retract when shield 814 deploys. Optionally, needle 704 is retracted into a housing 724 needle 704 and/or protected when shield 814 is withdrawn and/or compromised. Optionally when shield 814 is withdrawn and/or compromised, needle 704 may retract to inside a housing 724. For example, a housing may surround, partially surround and/or protect an inner space. Optionally or additionally a medicine to be injected may be stored on the inside of an injector.

Figure 9:
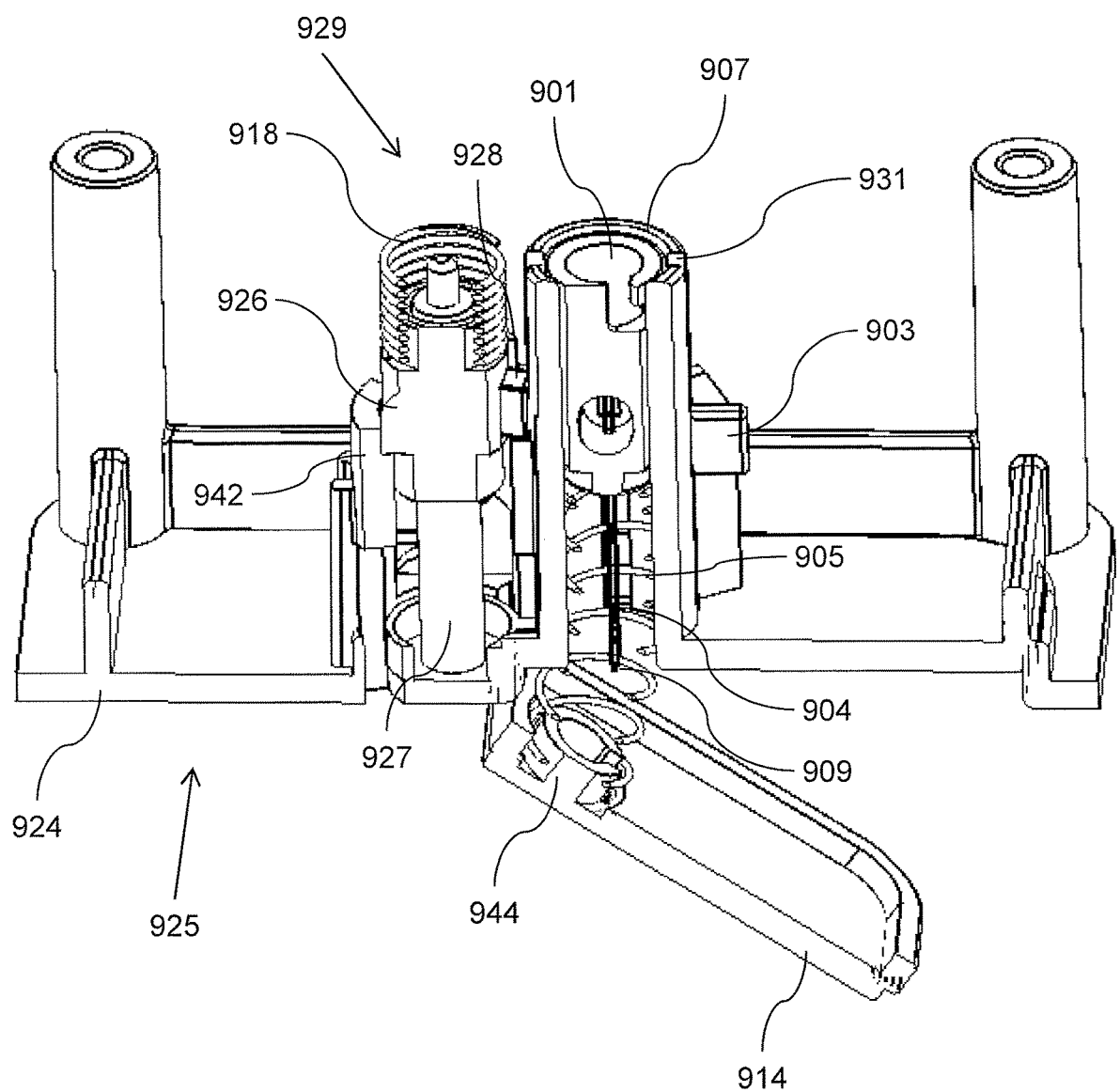
FIG. 9 is a perspective cutaway cross sectional illustration of a multistate needle insertion and protection system in a preactivated state in accordance with an embodiment of the current invention.
Figure 13A:
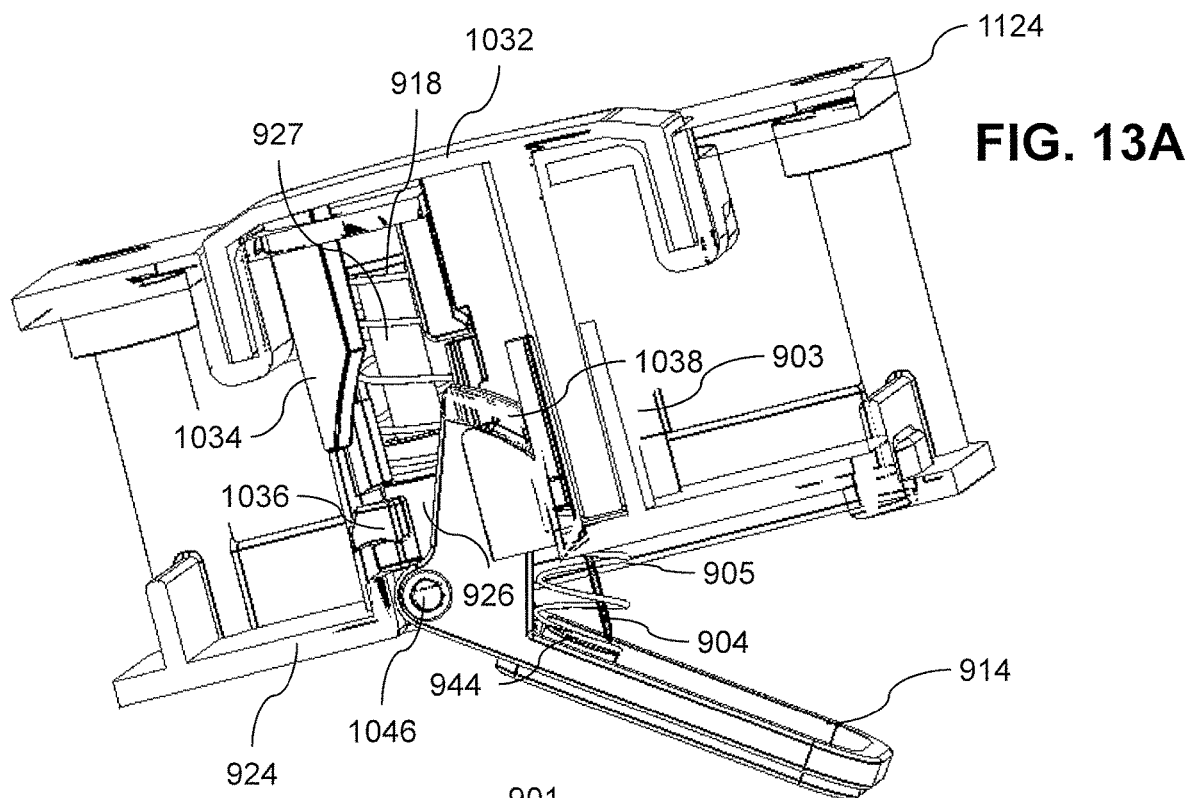
FIGS. 13A-13C are perspective cutaway illustrations of a mechanism holding a needle in an intermediate state in accordance with an embodiment of the current invention.
Figure 13B:
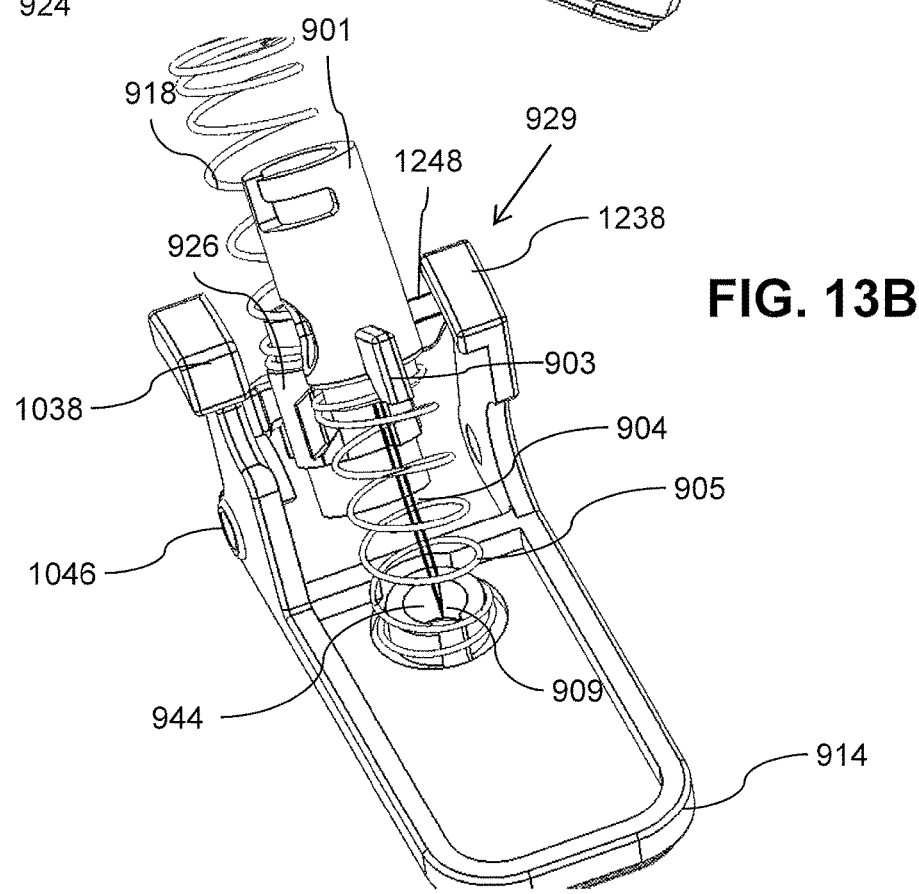
Figure 13C:
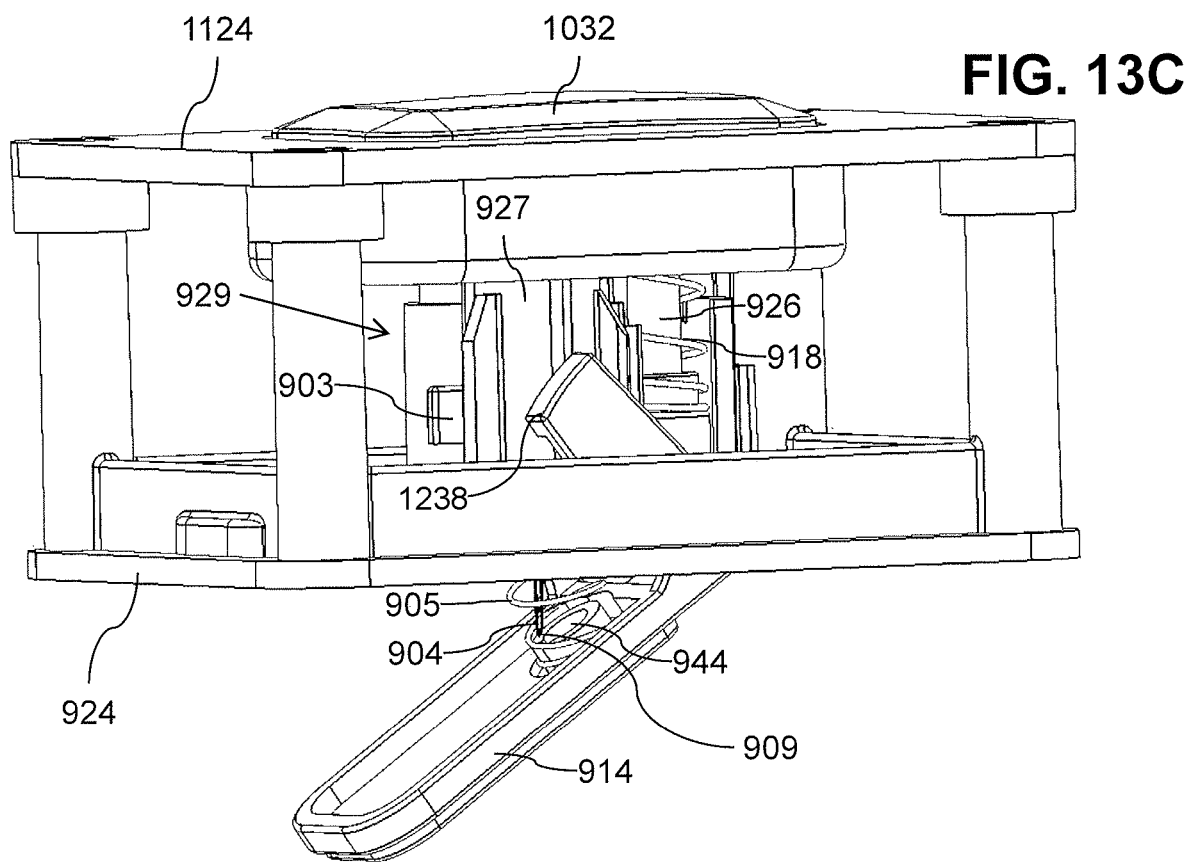

FIG. 9 is a perspective cutaway cross sectional illustration of a multistate needle insertion and protection system in accordance with an embodiment of the current invention. The system includes a tube (e.g. a hypodermic needle 904 with a tip 909 that is optionally sharpened) mounted on a needle retainer 901. Retainer 901 optionally moves along a path. For example the path may be defined by a cylindrical track 907 between a retracted position (for example as illustrated in FIG. 9-FIG. 11C) and/or an extended position (for example as illustrated in FIGS. 12A-12D) optionally including an intermediate, partially retracted position (for example, as illustrated in FIGS. 13A-13C).

In some embodiments a needle may be connected to a fluid train. For example, a needle may have a sharp point and/or a lumen. An opening to the lumen may be connected to the fluid train. For example, the fluid train may supply a connection between the lumen of a needle and a medicine cartridge. For example, the fluid train may be connected to and/or be in fluid communication with the lumen. For example, the fluid train may be connected to the needle or tube on an end opposite a sharpened end and/or opposite an end that is configured for contacting a subject and/or penetrating a skin of a subject.

In some embodiments, in the retracted position, needle 904 is located in a protected position. For example, in FIG. 9 a sharp tip of needle 904 is pulled back behind a contact surface 925 of base 924 of the device. Optionally, in the retracted position the entire needle 904 and/or a sharp tip thereof is surrounded by a housing. For example, in FIG. 9, needle 904 is surrounded by track 907.

In some embodiments a shield 914 is provided. Shield 914 optionally moves between a deployed position and a withdrawn position. An exemplary deployed position is illustrated in FIG. 9 wherein a portion of shield 914 is extended outward from contact surface 925. Optionally in the deployed position, a needle aperture 944 is disaligned with needle 904, for example, inhibiting extension of needle 904 past shield 914 (for example as illustrated in FIG. 13A). Optionally when shield 914 is in a withdrawn position aperture 944 is aligned with needle 904, for example allowing extension of needle 904 (for example as illustrated in FIG. 12C).

In some embodiments, a drive system 929 controls movement of needle 904. Optionally, drive system 929 includes an insertion mechanism. For example an insertion mechanism may cause a discharge tube (e.g. needle 904) to move outward and/or to protrude outward from skin contact surface 925 and/or to penetrate the skin of a subject. Alternatively or additionally drive system 929 includes a retraction mechanism that returns a discharge tube backwards from a protruding position towards a position behind contact surface 925. For example, in the embodiment of FIG. 9 a drive system 929 includes both an insertion and a retraction mechanism.

In some embodiments, drive system 929 includes a path defining element. For example a track and/or a carriage running along the track and/or a hinge and/or an axle and/or a selective movement blocking element. For example drive system 929 include track 907 and a carriage that runs along the track, for example a carriage may include a needle retainer 901. Optionally, needle retainer 901 slides along an inner bore of track 907 defining a linear path of movement of needle 904. For example in system 929, track 907 has a circular bore. Optionally, rotation alignment of retainer 901 is controlled via a tab 903 of retainer 901 moving along a slit 931 in track 907. Optionally slit 931 is linear to keep retainer 901 at a fixed rotational orientation. Alternatively or additionally, a slit may include a curve and/or a selective blocking elbow to cause rotation of a carriage and/or selectively block movement of a carriage dependent on its rotation orientation. Optionally slit 931 is blocked at a bottom point to limit movement of needle retainer 901 and/or to limit protrusion of needle 904. Optionally, tab 903 may include an indicator of needle position. For example an optical sensor may be used to track the position of tab 903 and/or needle 904.

In some embodiments, drive system 929 includes a second track 927 and carriage (e.g. driver 926). For example, driver 926 slides over track 927 along a linear path of movement. For example, selective movement blocking element 942 selectively blocks downward movement of driver 926 dependent on the rotational orientation of driver 926. Optionally, a track may define a linear and/or a curved path of movement. In some embodiments, a needle may have a linear and/or curved path of movement. Alternatively or additionally, a needle may move on an arm mounted on a pivot and/or another path determining mechanism. Alternatively or additionally, locking and/or facilitating and/or limiting of movement may be controlled by mechanisms other than rotational alignment. For example, a needle and/or needle mount and/or needle driver and/or needle retainer may include a locking mechanism with an elastic element and/or a lock (for example a barb and/or an interference element).

Figure 10:
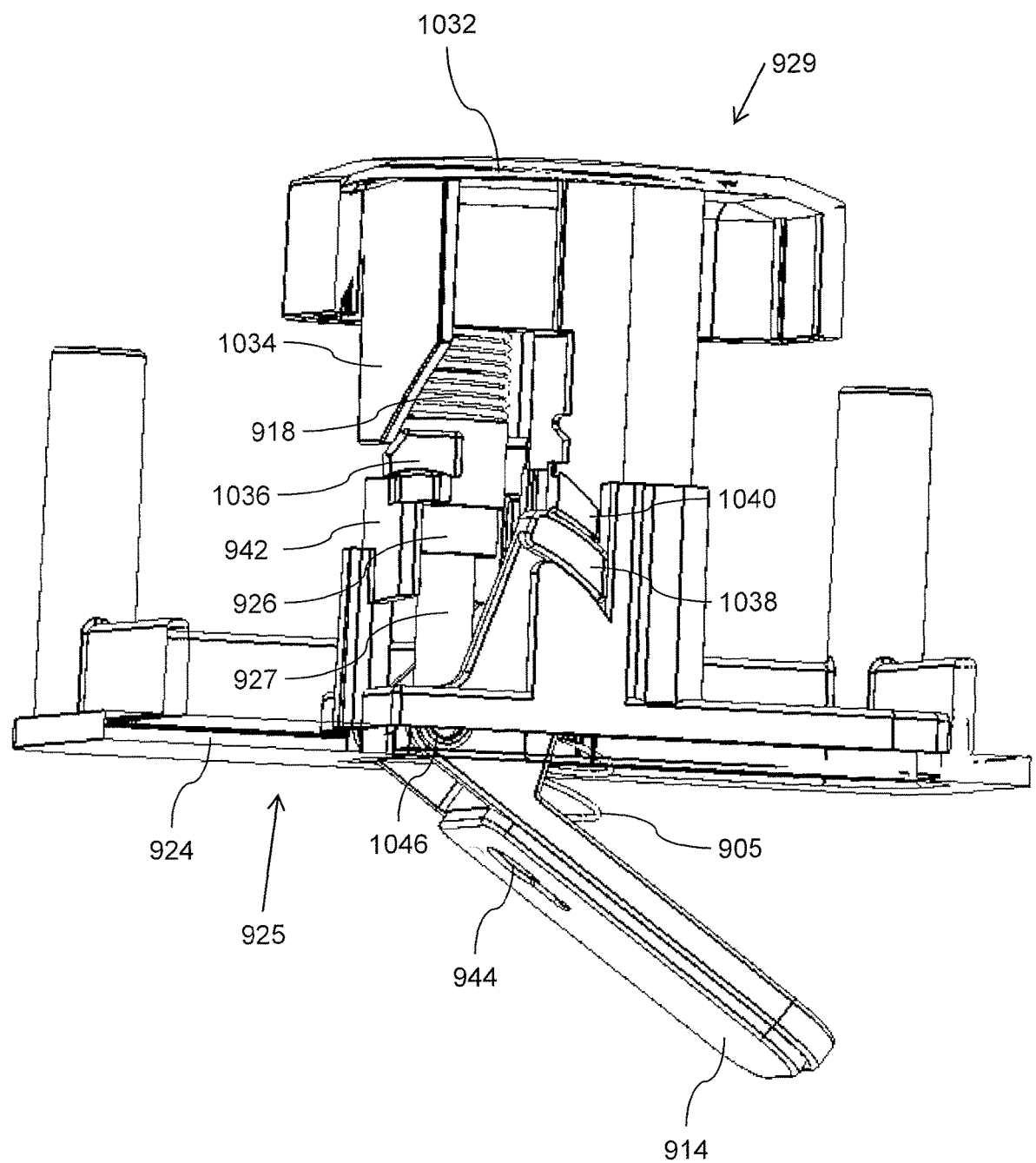
FIG. 10 is a perspective cutaway cross sectional illustration of a mechanism holding a needle in a preactivated state in accordance with an embodiment of the current invention.

Optionally, drive system 929 includes one or more energy storage device and/or actuators and/or forcing elements. For example, drive system 929 includes three forcing elements: a forced biased insertion spring 918, a backward biased shield actuator and/or retraction spring 905 and a manual actuator (for example a manual actuator may include a push button 1032 as illustrated in FIG. 10). Alternatively or additionally, an actuator and/or energy storage device may include an elastic element and/or an electrical actuator and/or a battery and/or a pressure reservoir and/or a pneumatic actuator and/or a hydraulic actuator and/or a chemical reservoir and/or a chemically reaction driven actuator.

In some embodiments, a drive system includes one or more control elements. Optionally, control elements may include interconnected moving elements that block and/or trigger movement of a needle and/or a needle shield and/or an actuator. A control element is optionally interconnected to and/or responsive to a sensor. For example, control elements may include a gear and/or a wheel and/or a friction element and/or an interference element and/or a flange and/or a rotating element and/or a sliding element. Alternatively or additionally, control elements may include a switching element and/or a logical processor. For example, a sensor may include a mechanical sensor interlocked with a mechanical control element. Alternatively or additionally, a sensor may include a mechanical sensor interlocked with a logical control element, for example a transducer and/or a processor. Alternatively or additionally a sensor may include other forms of sensors and/or transducers for example an optical sensor and/or a pressure transducer and/or a heat transducer. Interconnections between control elements may include mechanical connections, wired electrical connections, flow paths, and/or wireless connections.

In some embodiments, drive system 929 includes interconnected control elements. Optionally the drive elements are mechanically interlocked. For example, mechanical control elements of drive system 929 include a driver 926. For example, driver 926 may be actuated by spring 918 and/or include an interference element 928. For example, interference element 928 interconnects between needle driver 926 and needle retainer 901. In the exemplary embodiment, mechanical control elements of drive system 929 may be connected to and/or responsive to a mechanical skin sensor. For example, a skin sensor may include a shield 914. Optionally, shield 914 is deployed outward from surface 925 by spring 905. Optionally, shield 914 is interconnected to needle retainer 901 and/or button 1032 and/or driver 926. For example, mechanical control elements of drive system 929 including needle retainer 901 which is optionally biased inward from surface 925 by spring 905 may be interconnected to shield 914.

FIG. 10 is a perspective cutaway cross sectional illustration of a mechanism holding a needle in a preactivated state in accordance with an embodiment of the current invention. In some embodiments, in the preactivated state a sensor is activated and/or waiting to sense placement on a surface. For example, needle shield 914 may include a mechanical sensor that is deployed outward from surface 925 (for example as illustrated in FIG. 10). Optionally, in the preactivated state, activation button 1032 and/or needle 904 and/or driver 926 are locked in an inactivated and/or retracted state. For example, locking may inhibit premature extension of needle 904.

In some embodiments, a skin sensor element (e.g. shield 914) is interconnected to a control element and/or an actuator of driver system 929. For example interlocking may inhibit premature needle extension. For example, shield 914 interconnects to button 1032. For example, an interference element (e.g. a flange 1038) is integrated to shield 914. When shield 914 is in the deployed position, flange 1038 optionally blocks downward movement of a corresponding interference element (e.g. protrusion 1040) integrated to button 1032. For example, depression of button 1032 and/or activation of the device may be inhibited until the sensor detects placement on a surface.

In some embodiments, in the preactivated state, a control element is interlocked to a path defining element. For example, an interference element of driver 926 (e.g. protrusion 1036) may be interlocked to a selective blocking element 942. For example, the interlocking may inhibit downward movement of driver 926 and/or inhibit driver 926 from pushing needle retainer 901 and/or needle 904 outward. An exemplary 3-D form of protrusion 1036 is illustrated in more detail in FIGS. 11A and 12A. Button 1032 optionally includes a transmission element (e.g. wedge 1034) that transforms a force in a first direction on button 1032 to a force in a second direction on driver 926. For example, a downward force on button 1032 is transformed to a sideways force on protrusion 1036 and/or a torque on driver 926.

In some embodiments shield 914 rotates around a pivot 1046 for deployment away from surface 925 and/or withdrawal towards surface 925. In some embodiments, shield 914 includes an aperture. When shield 914 is deployed aperture 944 is optionally misaligned with needle 904 such that the point of needle 904 is blocked by shield 914.

Figure 11A:
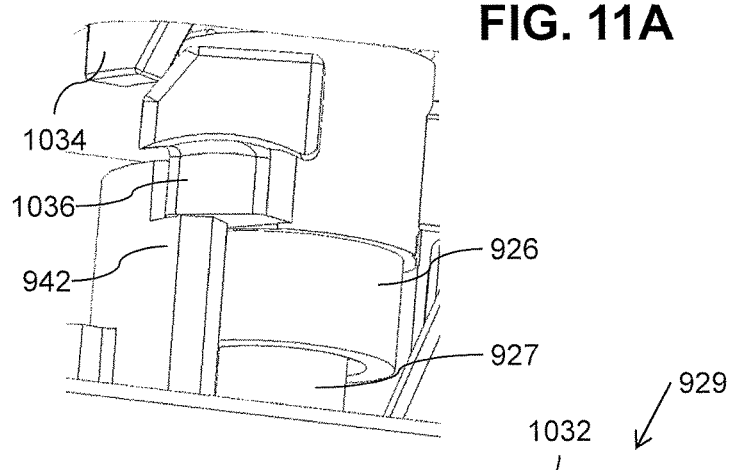
FIGS. 11A-11C are a perspective cutaway and cross sectional illustrations of a needle mechanism in a primed state in accordance with an embodiment of the current invention.
Figure 11B:
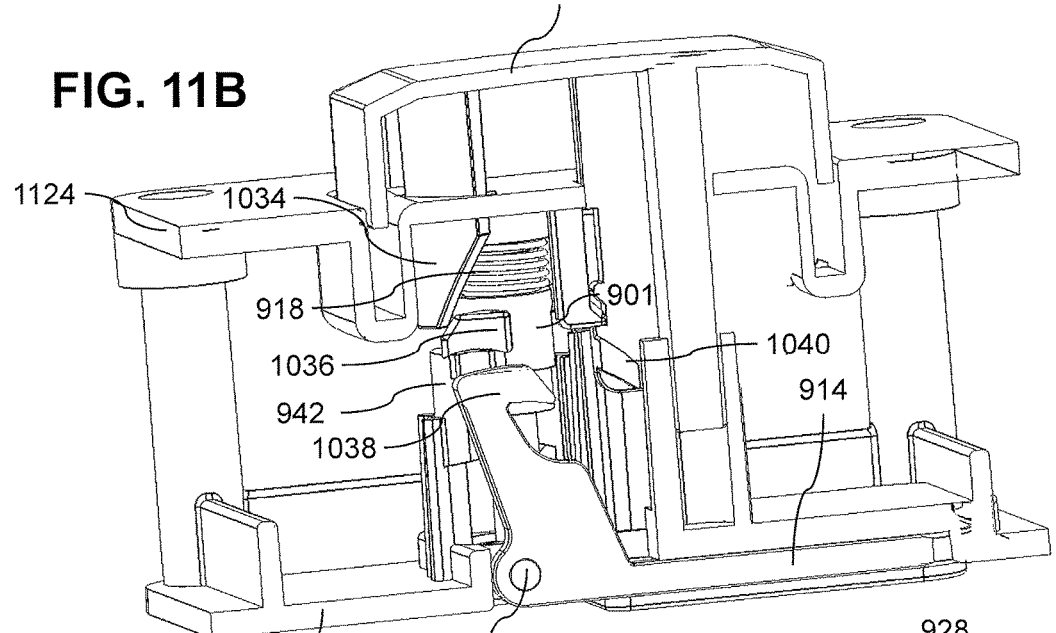
Figure 11C:
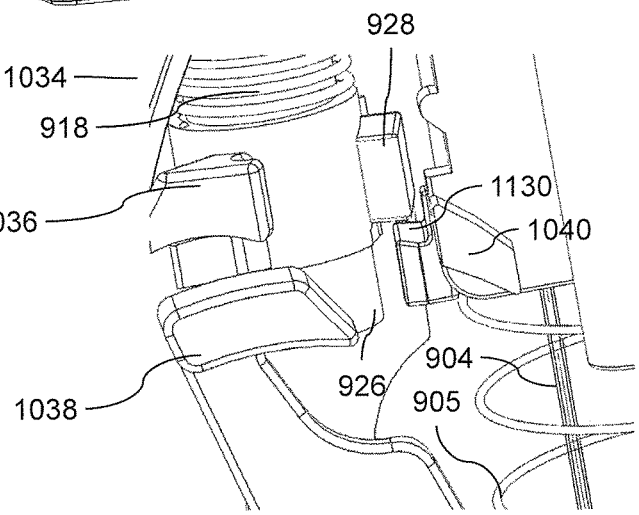
Figure 12D:
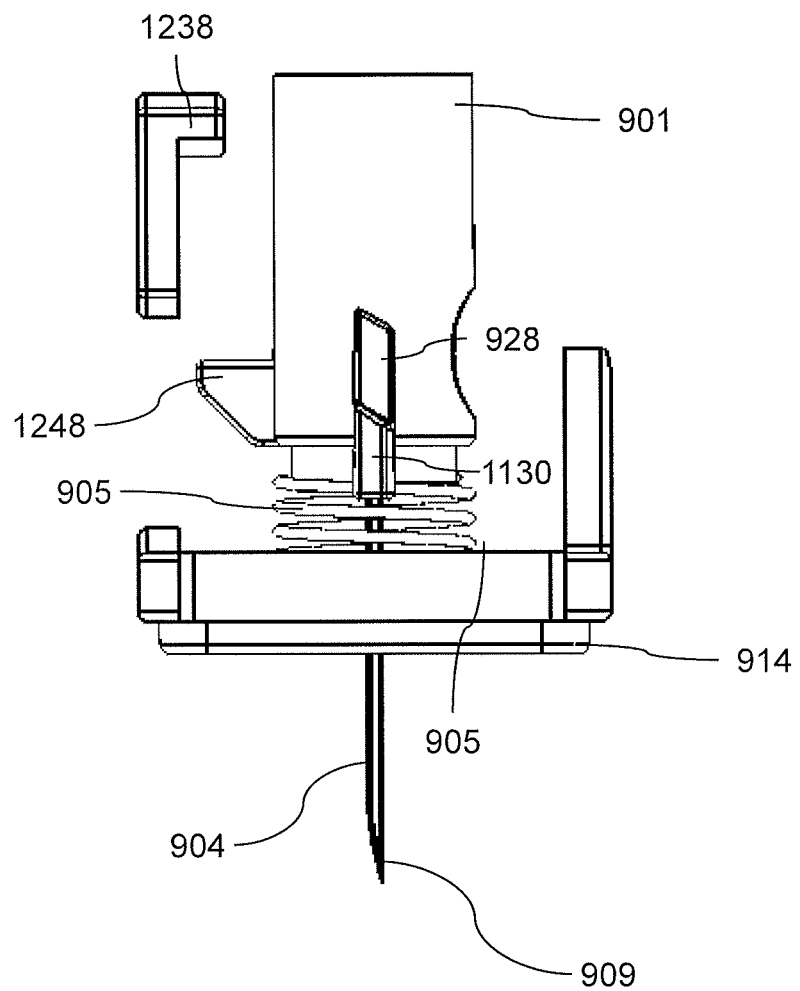

FIGS. 11A-11C are a perspective cutaway and cross sectional illustrations of a needle mechanism in a primed state in accordance with an embodiment of the current invention. In some embodiments, placing a preactivated drug delivery device against a surface primes the device. For example, placing contact surface 925 against the skin causes a skin sensor to register the skin and/or prime the device. For example, in the preactivation state, when surface 925 is placed against a surface, shield 914 is collapsed inward towards surface 925 from a deployed state optionally compressing spring 905 (for example as illustrated in FIG. 10). For example in FIG. 11B, shield 914 is illustrated collapsed. In some embodiment, shield 914 moves by rotation 1046 approximately 10 degrees around axis. Optionally in the collapsed state the outer surface of shield 914 is approximately flush with surface 925. For example, collapse of shield 914 causes flange 1038 to move out of the way of protrusion 1040 allowing button 1032 to be depressed. Optionally, depressing button 1032 releases a control element automatically activating the device. In some embodiments, rotation of a shield may range between 0 to 10 degrees and/or between 10 to 30 degrees and/or between 30 to 60 degrees and/or between 60 to 90 degrees and/or between 90 to 120 degrees and/or between 120 to 180 degrees.

In some embodiments, a transmission element of an actuator is aligned with an interference element of a control element. For example, in a primed state, wedge 1034 of button 1032 is aligned with protrusion 1036, for example as illustrated in FIG. 11A. Optionally, depressing button 1032 will push wedge 1034 against protrusion 1036. As wedge 1034 is pushed against protrusion 1036, it optionally transmits a lateral force onto protrusion 1036. For example, the lateral force may cause a torque on driver 926 (for example due to the force couple between the driving force of wedge 1034 on protrusion 1036 and the counter force of track 927). The torque will optionally rotate driver 926 around track 927. Rotating driver 926 optionally disengages protrusion 1036 from blocking element 942, for example as illustrated in FIGS. 11A-11C.

In some embodiments, rotating drive 926 aligns an interference element 928 with a corresponding interference element 1130 on needle retainer 901, for example as illustrated in FIG. 11C.

In some embodiments, a drug discharge device includes an upper housing. For example, a portion of an upper housing 1124 is illustrated in FIG. 11B. Optionally a needle driver system may be completely surrounded by base 924 and/or upper housing 1124.

FIGS. 12A-12D are perspective cutaway and cross sectional illustrations of a needle mechanism in an activated and/or extended state in accordance with an embodiment of the current invention. In some embodiments, a user activates a device from a primed state to an active state. For example, by a user depressing button 1032, driver 926 is rotated, aligning interference element 928 of driver 926 with interference element 1130 of needle retainer 901 and/or disengaging protrusion 1036 from selective blocking element 942. When protrusion 1036 is disengaged from selective blocking element 942, spring 918 pushes driver 926 downward. As driver 926 moves downward interference element 928 optionally engages interference element 1130 and/or drives needle retainer 901 downward and/or extends needle 904 outward. Optionally driver 926 is held down by spring 918. Optionally, while shield 914 is in the withdrawn position and driver 926 is in the extended position, driver 926 is prevented from disengaging from needle retainer 901.

In some embodiments, in the active stage needle 904 is locked in the extended position. For example, needle 904 may extend into the skin of a subject and/or act as a fluid path for discharging the drug into the subject. Optionally, needle 904 may be locked in the extended position by driver 926. For example, interference element 928 may remain engaged to interference element 1130 preventing upward movement of needle retainer 901 and/or retraction of needle 904. For example, while shield 914 is in the withdrawn position, shield 914 engages protrusion 1036 and/or prevents driver 926 from rotating. As long as driver 926 is prevented from rotating, interference element 928 of driver 926 optionally remains engaged with interference element 1130 of needle retainer 901, for example as illustrated in FIG. 12A.

In some embodiments, while shield 914 is in the withdrawn position, aperture 944 is aligned with needle 904 allowing needle 904 to extend out aperture 944 as is illustrated for example in FIGS. 12B-12C.

FIG. 12A illustrates an optional interference element (e.g. a flange 1248) on needle retainer 901. Optionally, needle shield 914 includes an interference element (e.g. a lug 1238). For example, when shield 914 is in a withdrawn position (for example as illustrated in FIG. 12C) lug 1238 is not aligned with flange 1248. For example, when shield 914 is in a deployed position (for example as illustrated in FIG. 13A) lug 1238 is aligned with flange 1248.

FIGS. 13A-13C are perspective cutaway illustrations of a mechanism holding a needle in an intermediate state in accordance with an embodiment of the current invention. In some embodiments, when the base 924 is removed from an injection surface (e.g. the skin of a subject), shield 914 moves outward to the deployed position. For example shield 914 pivots outward around pivot 1046. Optionally outward movement of shield 914 facilitates retraction of needle 904. Additionally or alternatively, needle may partially retract and/or be held in a stable partially retracted position.

Figure 15:
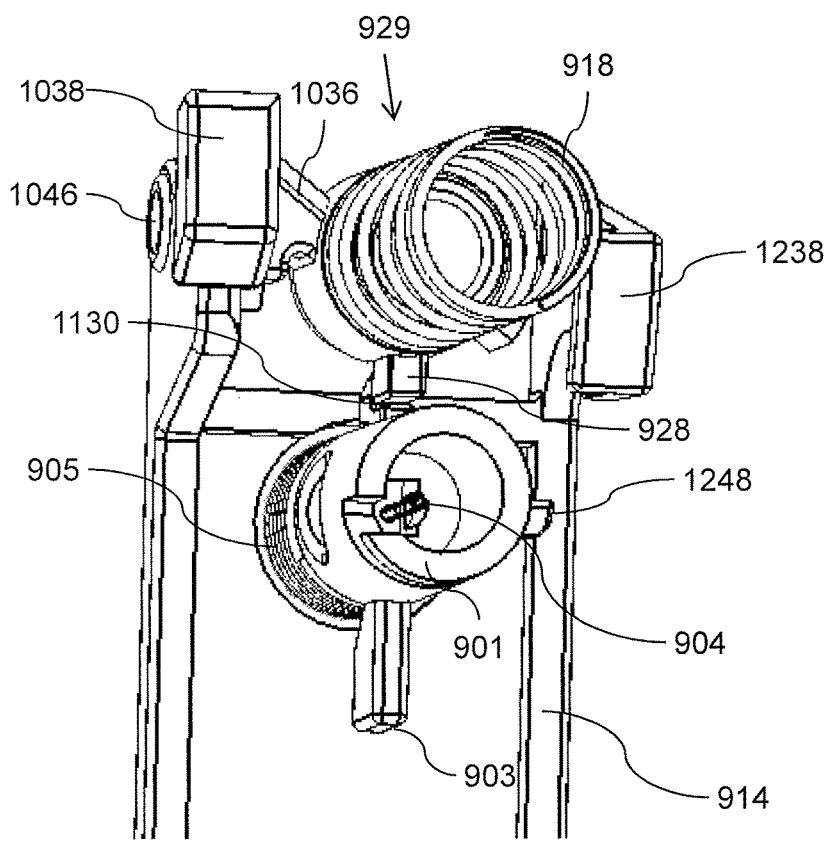
FIG. 15 is a perspective cutaway illustration of a mechanism in an activated state in accordance with an embodiment of the current invention.

In some embodiments, in the active state, driver 926 is biased to disengage from needle retainer 901. For example, in the active state driver 926 is biased to rotate by the force of spring 905 against the angled interface between interference element 928 and interference element 1130. In the active state disengagement is optionally blocked by interference between shield 914 and protrusion 1036, for example as explained in regards to FIG. 12A and as illustrated in FIG. 15.

In some embodiments, deploying of shield 914 from a withdrawn state in an active state to a deployed state (for example by removing the injector from the skin of a subject) unlocks needle 904 and/or or facilitates needle retraction. Optionally, deploying shield 914 from the active/withdrawn state frees driver 926 to rotate. For example, as illustrated in FIGS. 12A and 15, in the active state, shield 914 interferes with movement of protrusion 1036 and/or inhibits rotation of driver 926. Optionally, as can be seen for example in FIGS. 13A and 16, when shield 914 is deployed, the body of shield 914 is distanced from protrusion 1036 enough to not interfere with rotation and/or to allow rotation of protrusion 1036 and/or driver 926.

Optionally, when driver 926 rotates from the active position (for example of FIG. 15) to the partial retracted position (for example of FIG. 16) interference elements 928 and 1130 disengage. Disengaging interferences element 928 allows interference element 1130 and/or needle retainer 901 and/or needle 904 to move inward (e.g. retract).

In some embodiments, while shield 914, is in the deployed position, needle 904 retracts to and/or is held in the partially retracted position. For example as illustrated in FIG. 13B, shield 914 may be integrated to an interference element or flange (e.g. lug 1238). When shield 914 is deployed, interference lug 1238 optionally blocks a retraction path of needle 904. For example, lug 1238 blocks retraction of needle 904 before it reaches a fully retracted position (for example before it reaches the fully retracted state illustrated in FIGS. 9-11C). For example, as needle 904 retracts flange 1248 contacts lug 1238 stopping retraction in the partially retracted state. Optionally, while shield 914 remains in the deployed state, needle 904 is held stable in the partially retracted state.

In some embodiments, in the deployed position, shield 914 covers a tip of needle 904. For example, in the deployed position aperture 944 may be misaligned with needle 904 (for example as illustrated in FIGS. 13A and 13C). For example, in the extended and/or partially retracted position, needle 904 may block shield 914 from withdrawing from the deployed position to the withdrawn position. Optionally, shield 914 may be positioned very close to the tip of needle 904. For example, close positioning of shield 914 over needle 904 may inhibit insertion of a finger between shield 914 and needle 904 may inhibit a stick hazard.

Optionally, for example as illustrated FIG. 13C, in the intermediate state a portion of needle 904 may extend out of base 924. For example, in the intermediate state needle 904 may protrude from base 924 less than in the active state. Optionally, in the intermediate state the needle may be protected, for example by shield 914.

Figure 14:
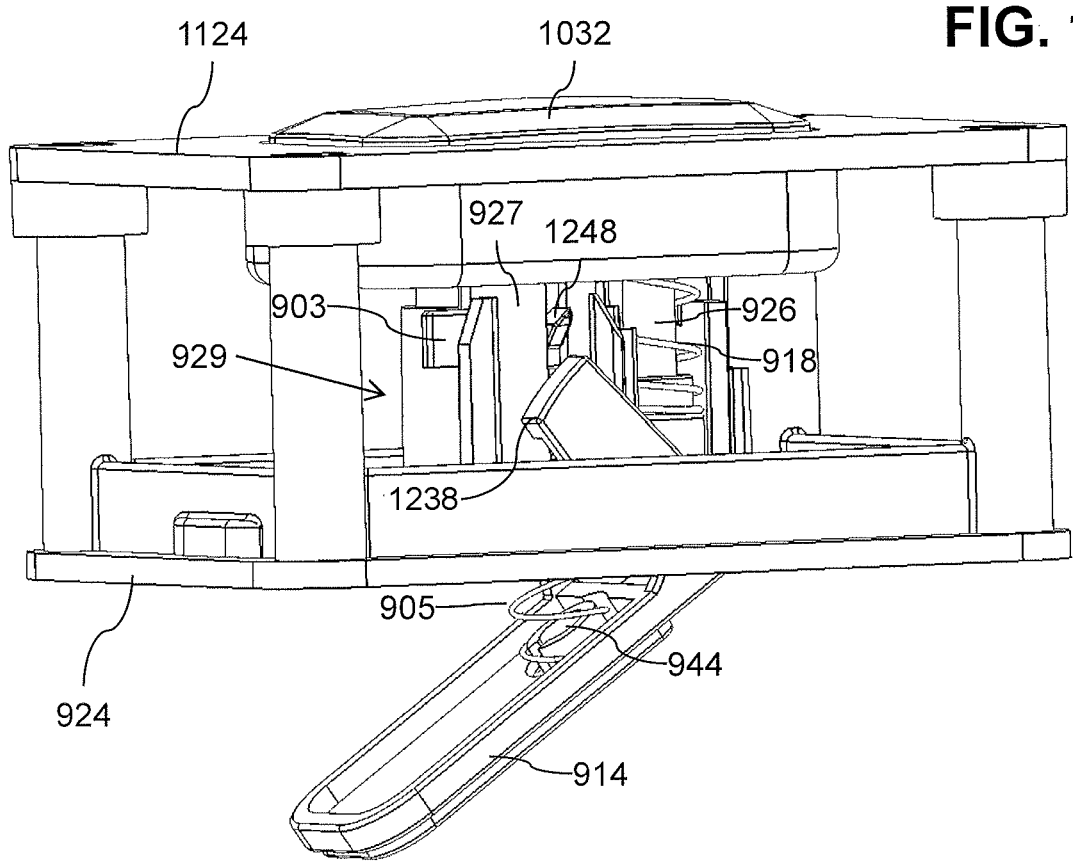
FIG. 14 is a perspective cutaway illustration of a mechanism holding a needle in a retracted state in accordance with an embodiment of the current invention.

FIG. 14 is a perspective cutaway illustration of a mechanism holding a needle in a retracted state in accordance with an embodiment of the current invention. In some embodiments, disturbing shield 914 in the deployed position may cause needle 904 to collapse from an intermediate position to a further and/or fully retracted position. For example when shield 914 moves, flange 1038 may disengage from flange 1248. Disengagement of flange 1038 from flange 1248 may allow needle 904 to retract. Optionally, retraction may be driven by an actuator, for example spring 905. Alternatively or additionally, needle 904 may be freed to retract such that collapse of shield 914 from the deployed to the withdrawn position may push needle 904 and or further retract the needle. For example, shield 914 is pushed towards base 924 needle 904 may retract to a protected position inside of housing 1124.

FIG. 15 is a perspective cutaway illustration of a needle mechanism in an activated state in accordance with an embodiment of the current invention. Optionally in the activated state, needle 904 is held in an extended state by needle holder 901. For example, needle holder 901 is held in the extended position by contact between an interference elements on driver 926 (e.g. interference element 928) and retainer 901 (e.g. interference element 1130). In turn, driver 926 is optionally held extended towards the base of the device by an actuator (e.g. spring 918). Interference element 928 optionally is kept engaged with interference element 1130 by interference between a protrusion 1036 on driver 926 and shield 914 (e.g. protrusion 1040 and the portion of shield 914 to which it is attached).

Figure 16:
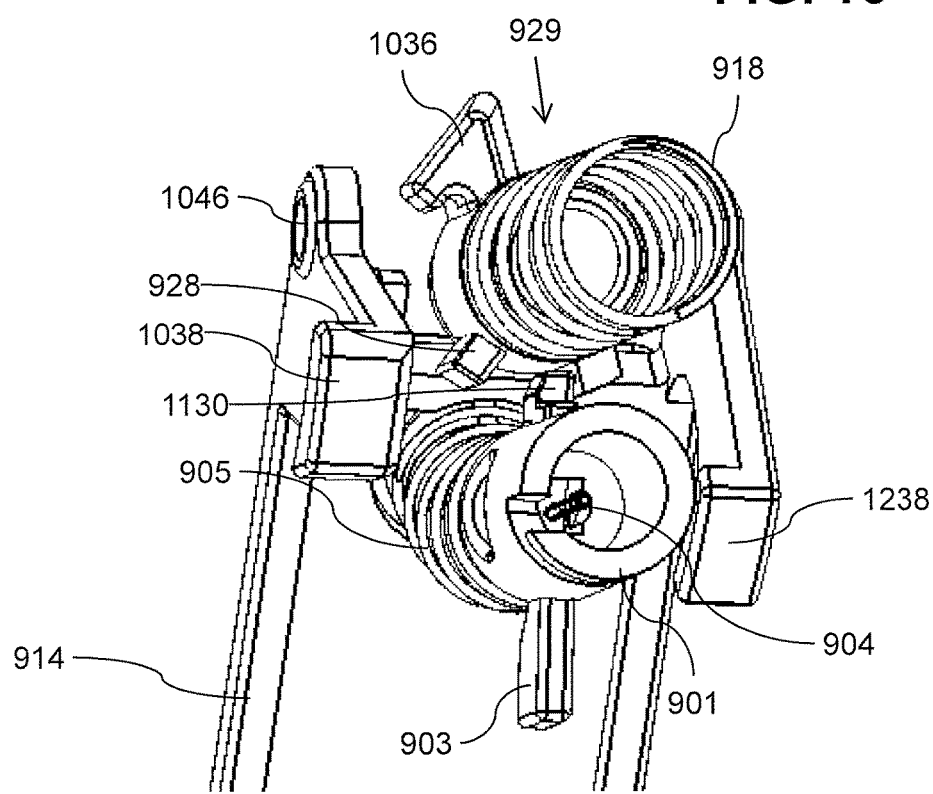
FIG. 16 is a perspective cutaway illustration of a mechanism holding a needle in an intermediate state in accordance with an embodiment of the current invention.

FIG. 16 is a perspective cutaway illustration of a mechanism holding a needle in an intermediate state in accordance with an embodiment of the current invention. In some embodiments, when the device is removed from a surface, shield 914 pivots outward. Movement of shield 914 optionally allows further retraction of needle 904. For example, pivoting of shield 914 ends interference between protrusion 1036 and the extension of shield 914. Without interference between protrusion 1036 and shield 914, driver 926 optionally rotates. For example, as illustrated in FIG. 16, rotation of driver 926 disaligns interference element 928 from interference element 1130 optionally allowing interference element 1130 and/or needle retainer 901 and/or needle 904 to retract. Optionally, needle retraction is stopped at an intermediate position for example as described above with respect to FIG. 13C, by interference between flange 1248 of needle retainer 901 and lug 1238 of shield 914.

Figure 17:
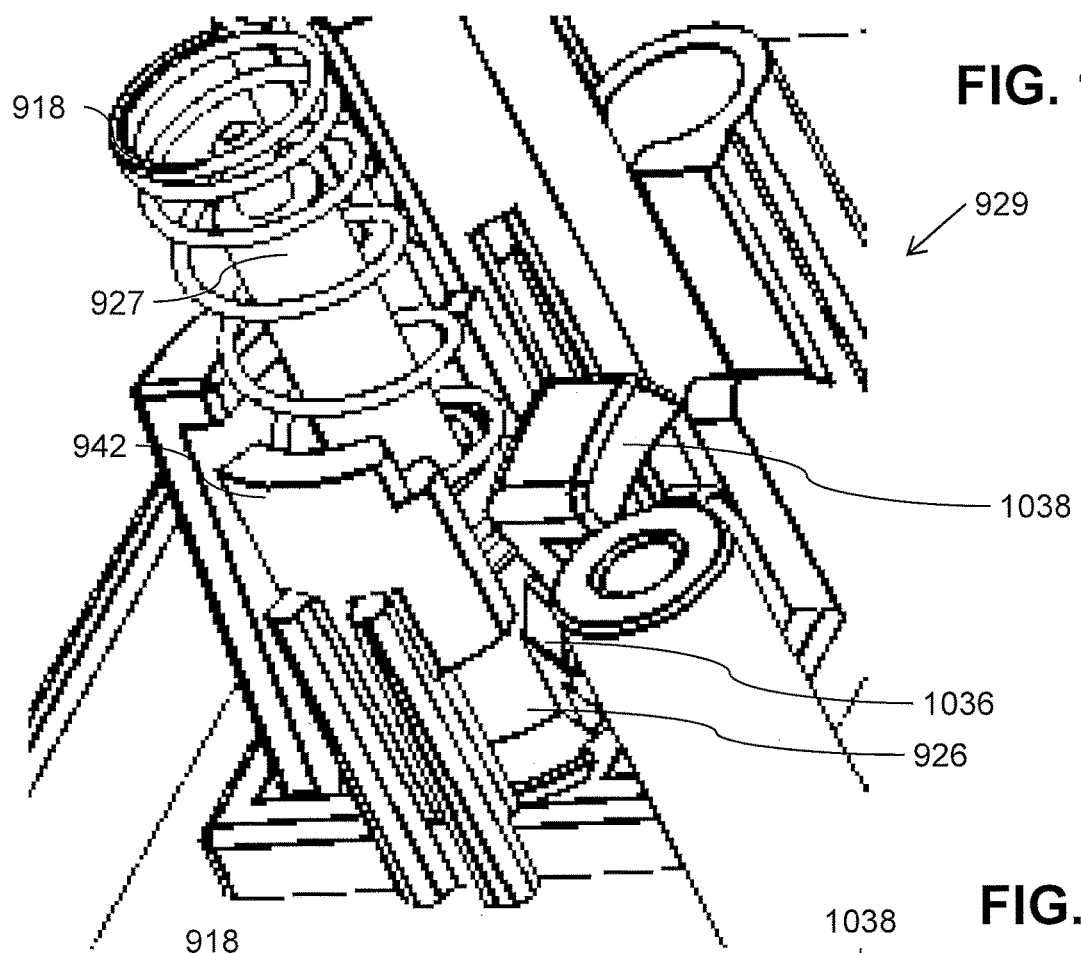
FIG. 17 is a perspective cutaway illustration of a mechanism in an active state in accordance with an embodiment of the current invention.

FIG. 17 is a perspective cutaway illustration of a mechanism holding a needle in an extended state in accordance with an embodiment of the current invention.

Figure 18:
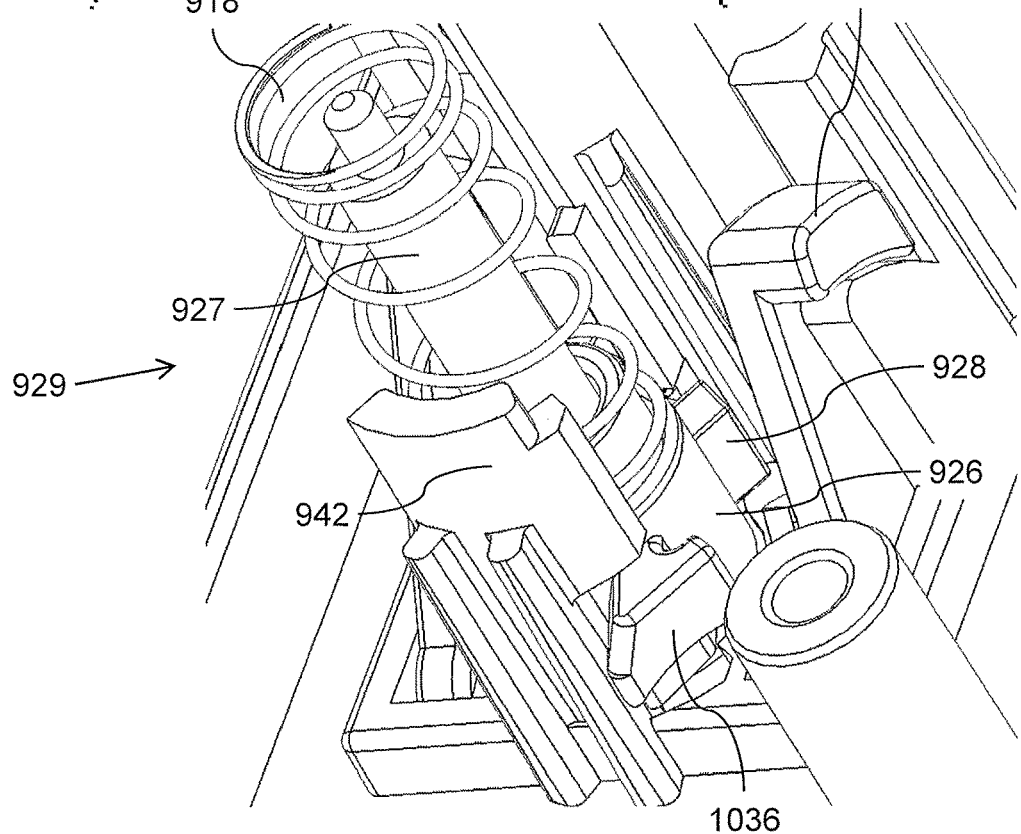
FIG. 18 is a perspective cutaway illustration of a mechanism holding a needle in an intermediate state in accordance with an embodiment of the current invention.

FIG. 18 is a perspective cutaway illustration of a mechanism holding a needle in an intermediate state in accordance with an embodiment of the current invention.

Figure 19:
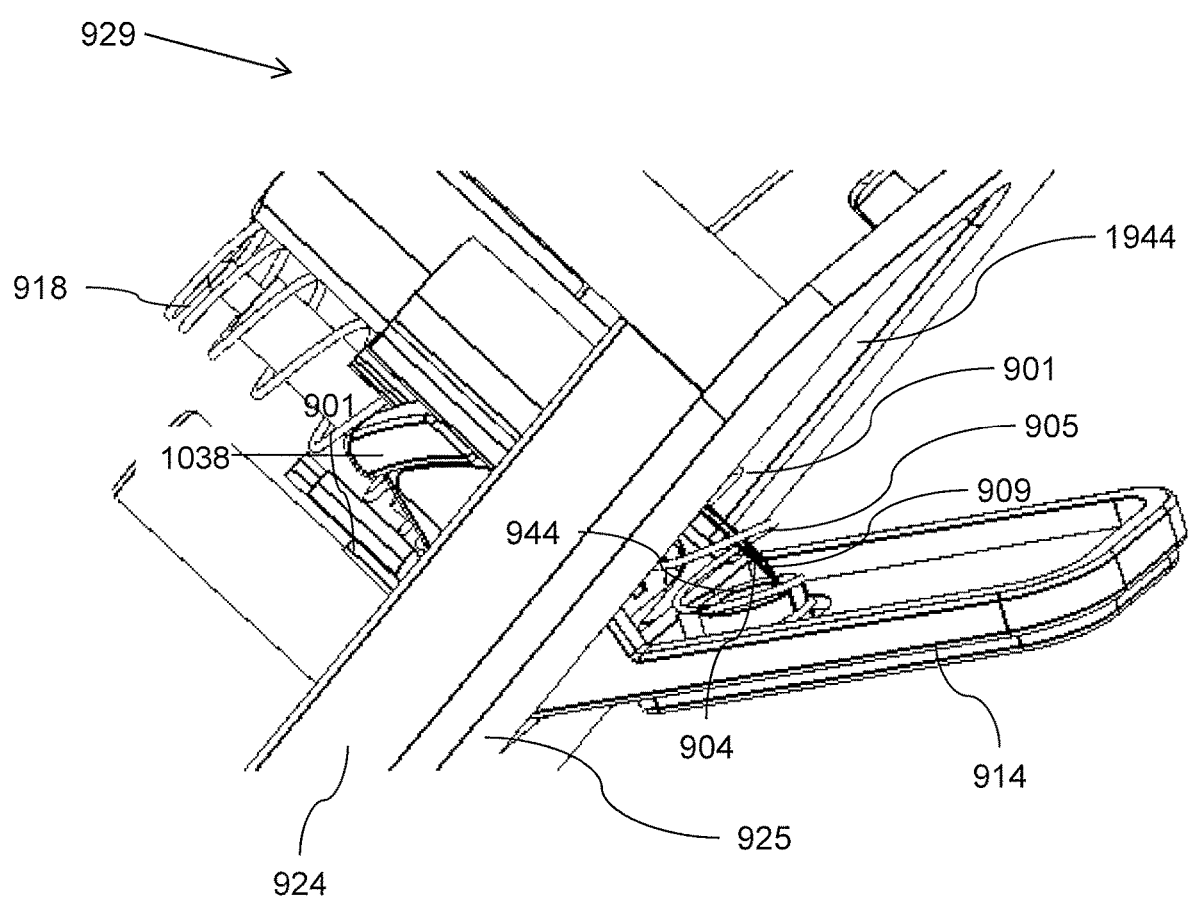
FIG. 19 is a perspective cutaway illustration of a mechanism holding a needle in an intermediate state in accordance with an embodiment of the current invention.

FIG. 19 is a perspective cutaway illustration of a mechanism holding a needle in an intermediate state in accordance with an embodiment of the current invention. In some embodiments needle shield 914 may include an aperture 944. Optionally when shield 914 is deployed, aperture 944 is disaligned with needle 904. For example, outward movement of needle 904 is blocked by shield 914 in the deployed position. Alternatively or additionally, in the partially retracted position, needle 904 may be locked, inhibiting outward movement.

In some embodiments, base 924 includes an opening 1944. Optionally in the withdrawn position, needle shield 914 covers opening 1944. For example in the withdrawn position, the outer surface of shield 914 may be approximately flush with surface 925. Alternatively or additionally, a base may have an indentation and/or shield 914 in the withdrawn position may fit into an indentation that does not penetrate through the base.

Figure 20:
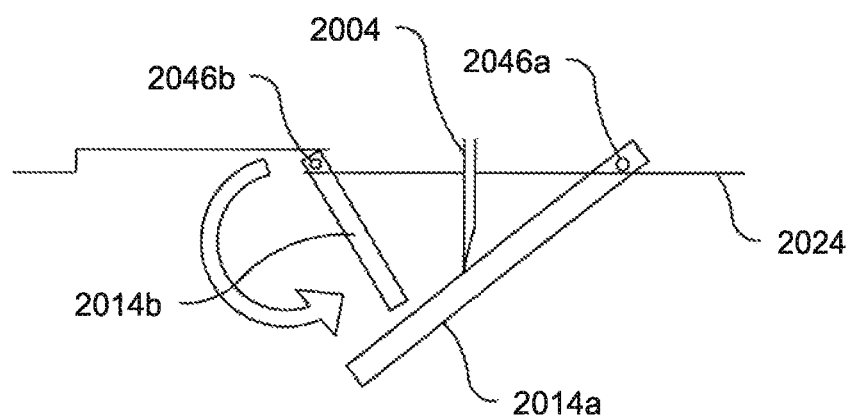
FIG. 20 is a schematic illustration of dual rotating needle shields in accordance with an embodiment of the current invention.

FIG. 20 is a schematic illustration of dual needle shields in accordance with an embodiment of the current invention. In some embodiments, a second needle shield may be used to fortify a first shield against movement due to external forces and/or to block access to a stick hazard. For example, a primary shield 2014a may cover a stick hazard. A secondary shield 2014b may prop up primary shield 2014a and/or block an opening between shield 2014a and a base 2024 of the device.

In some embodiments, a primary shield may rotate around a first axis 2046a. Optionally a secondary shield may rotate around a second access 2046b. For example, shield 2014a may lie in a withdrawn state over needle 2004 in a retracted state and may open by movement to an acute angle (e.g. counter clockwise in FIG. 20) overlying needle 2004. Alternatively or addition, shield 2014a may have a withdrawn position flat against base 2024, but not overlying the needle and/or may open (e.g. clockwise in FIG. 20) to an obtuse angle overlying needle 2004. For example, shield 2014b may lie in a withdrawn state not overlying needle 2004 in a retracted state. For example needle shield 2014b may open to an obtuse angle (e.g. counter clockwise in FIG. 20). Alternatively or addition, shield 2014b may have a withdrawn position overlying the needle and/or may open (e.g. clockwise in FIG. 20) to an acute angle.

Figure 21A:
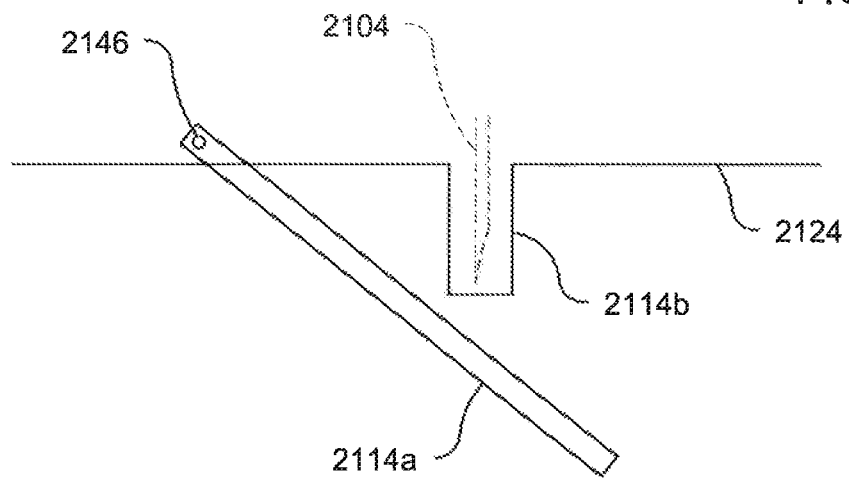
FIGS. 21A and 21B are schematic illustrations of a combination of rotating and translating needle shields in accordance with an embodiment of the current invention.
Figure 21B:
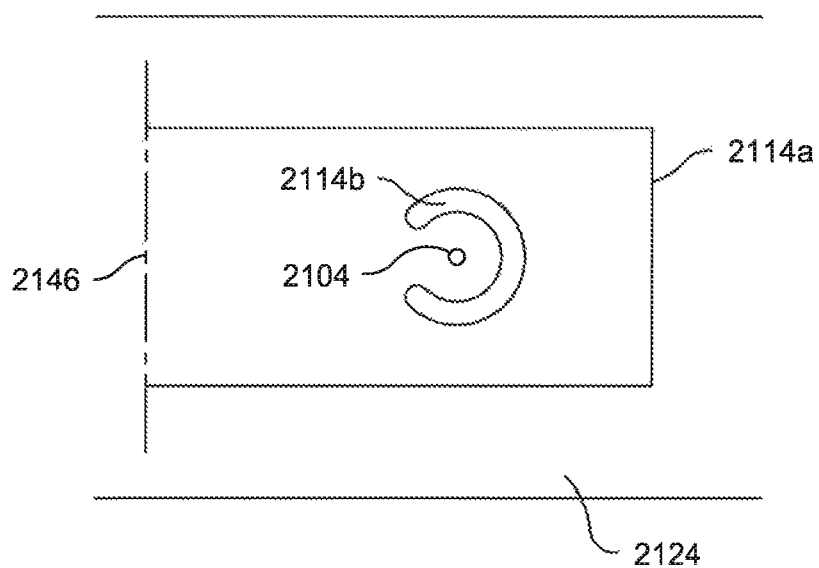

FIGS. 21A and 21B are schematic illustrations of needle protection mechanism including a translating needle shields in accordance with an embodiment of the current invention. In some embodiment, a needle shield may include a translating part. For example a sleeve 2114b may deploy by translating parallel to the axis of a needle. For example, sleeve 2114b may deploy by translating outward from a base 2124 to cover a needle. For example, shield 2114b deploy at the end of delivery of a drug and/or when the device is removed from the subject. Optionally sleeve 2114b may partially surround needle 2104. For example, as shown in FIG. 21B, shield 2114b surrounds needle 2104 on three sides. Alternatively or additionally, a sleeve may entirely surround a needle and/or shield a needle from one side. In some embodiments shield 2114b may lock open. Alternatively or additionally, shield 2114b may lock to needle 2104. For example when shield 2114b is locked to needle 2104, moving shield 2114b may also move needle 2104. For example, forcing shield 2114b inward (e.g. towards its withdrawn position) may also force needle 2104 inwards and/or retract needle 2104. Alternatively or additionally compromising shield 2114b (e.g. applying a force to shield 2114b) may trigger automatic retraction of needle 2104. In some embodiments a system with a translating shield 2114b may also include a pivoting shield 2114a, for example pivoting around a pivot 2146. Alternatively or additionally, a translating shield 2114b shields a needle without a pivoting shield. For example, shield 2114b may be pushed downward by a spring and/or pulled down by shield 2114a.

Figure 22:
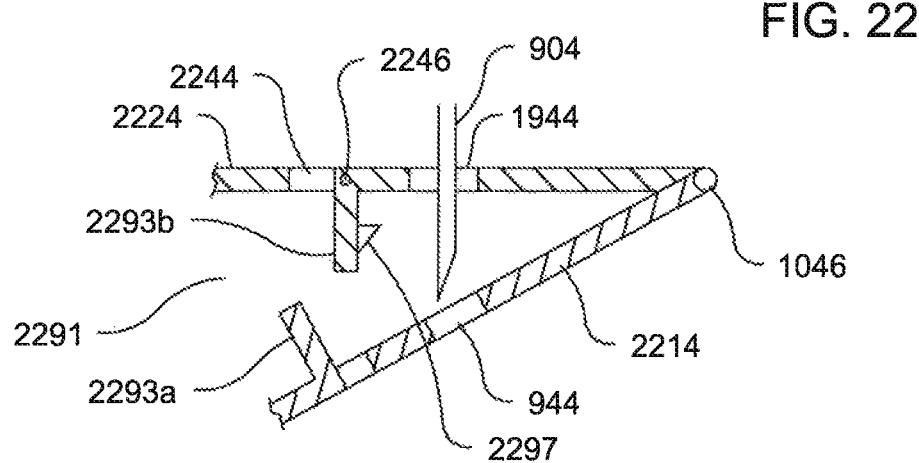
FIG. 22 is a schematic illustration of a needle protection latch in accordance with an embodiment of the current invention.

FIG. 22 is an illustration of a needle point protection device with a protrusion blocking a path to a needle point in accordance with an embodiment of the current invention. In some embodiments, a protection device may leave a path of access to a sharp hazard. For example, a needle shield 2214 may deploy shielding a needle point (for example such that the needle point is located between shield 2214 and a housing of the device (for example a base 2224)). In some embodiments a gap 2291 provides a path of access to the needle point and/or a path for potential exposure to the hazard. Optionally, a protrusion (for example protrusions 2293a and/or 2293b) blocks gap 2291. For example, protrusions 2293a and/or 2293b may be deployed and/or withdrawn.

In some embodiments, a protrusion may be deployed with a needle shield. For example, protrusion 2293a is integral to and/or connected to shield 2214 such that deploying shield 2214 to cover a tip of needle 904 automatically deploys protrusion 2293a to at least partially block gap 2291. Optionally a channel 2244 may be provided into which protrusion 2293a fits when it is withdrawn. For example, when shield 2214 is withdrawn, protrusion 2293a fits into channel 2244 in base 2224. Optionally, withdrawing shield 2214 and/or protrusion 2293a avoids interference by the shield with the functioning of the device. For example, when the device is active, shield 2214 is flush with base 2224 and/or protrusion 2293a is inserted into channel 2244 such that in the withdrawn state shield 2214 and/or protrusion 2293a do not interfere with contact between the outer side of base 2224 and the skin of the subject.

In some embodiments a path to a hazardous component may be blocked by a protrusion extending from a housing of a device. For example, protrusion 2293b at least partially blocks gap 2291. Optionally, multiple protrusions 2293a and 2293b may cooperate and/or intermesh to block gap 2291. In some embodiments, protrusion 2293b may be withdrawable. For example, when a device is placed on the skin of a user and/or in an active mode, protrusion 2293b may withdraw into base 2224, facilitating contact between base 2224 and the skin of a user. Optionally, when the device is removed protrusion 2293a deploys.

In some embodiments, a protrusion may include a sensor. Optionally, protrusion 2293b may sense a distance between base 2224 and a skin of a user (for example the distance may be the shortest distance from the base to a contact point on the sensor for example for shield 914 the distance to the skin may be operationally measured as the distance from the distance from the far end of shield 914 [opposite pivot 1046] to base 924 along a line perpendicular to the plane of base 924). For example, protrusion may be biased outward and/or be pushed inward by skin as base 2224 is placed on the skin. Optionally, a sensor (for example a linear gauge sensor) measures the distance that protrusion 2293b protrudes from base 2224. That distance may be a measure of the distance from a skin of the user. Optionally, protrusion withdraws when the device is placed straight onto skin, but locks when a force is applied towards needle 904. For example, if a user tries to push his finger in to gap 2291 towards needle 904, he will push protrusion 2293b rightward. The rightward force optionally locks protrusion 2293b in the protruding state. For example, the protrusion 2293b may be locked in the protruding state by a ratchet 2297 and/or a pivot 2246. For example, pivot 2246 may be biased clockwise, disengaging ratchet 2297 unless a significant force is applied rightward. Alternatively or additionally, pivot 2246 may allow protrusion 2293b to collapse in one direction (for example clockwise) which is not associated with a hazard (for example a finger penetrating gap 2291) and/or not in a second direction (for example counter clockwise) that is associated with a finger penetrating gap 2291.

Figure 23:
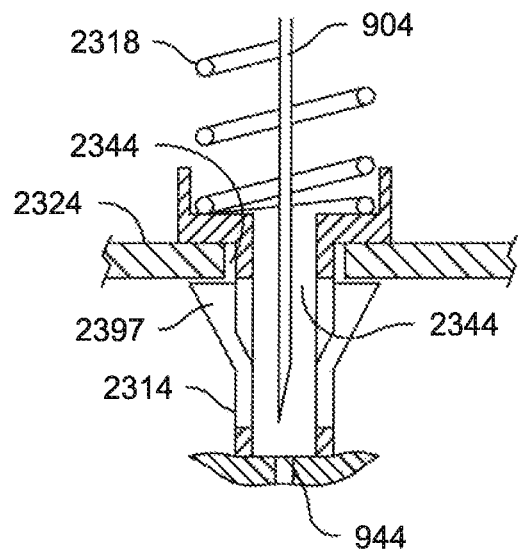
FIG. 23 is a schematic illustration of a translating needle shield in accordance with an embodiment of the current invention.

FIG. 23 is a schematic illustration of a needle protection device with a linear deploying needle shield in accordance with an embodiment of the present invention. Optionally a shield 2314 includes a tubular body and a locking mechanism (for example barbs 2397). Optionally, at the end of injection and/or when the device is removed from the skin of a recipient, an actuator (for example spring 2318) pushes shield 2314 out through needle hole 2344 in base 2324. For example, barbs 2397 lock shield 2314 in an extended position shielding needle 904.

Figure 24A:
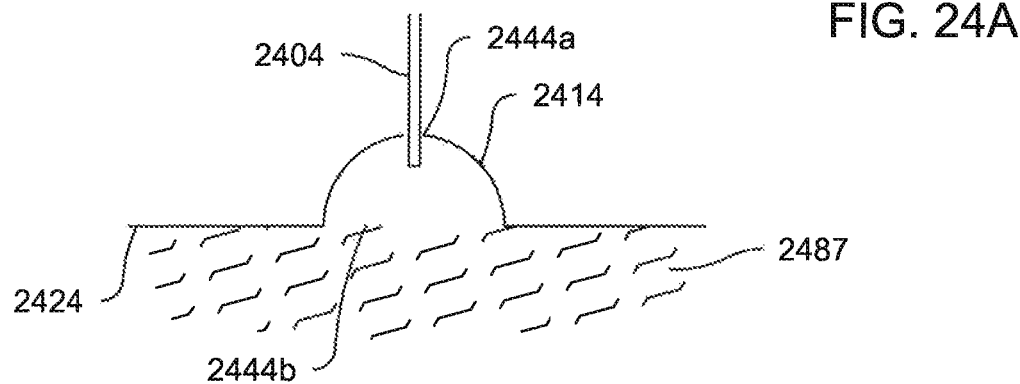
FIGS. 24A-24C are a schematic illustrations of a needle protection mechanism in accordance with an embodiment of the current invention.
Figure 24B:
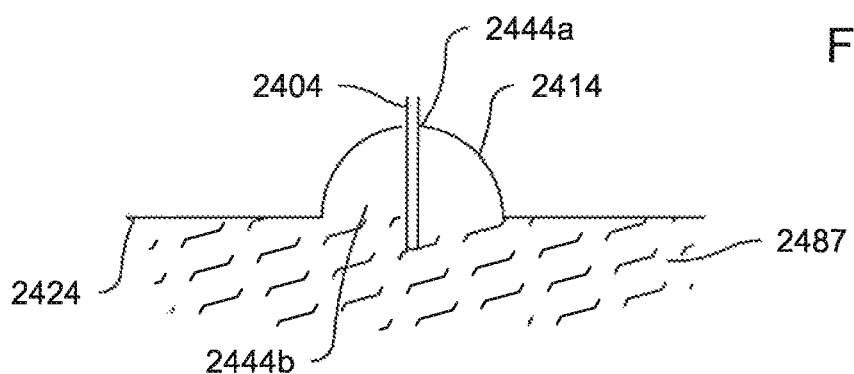
Figure 24C:
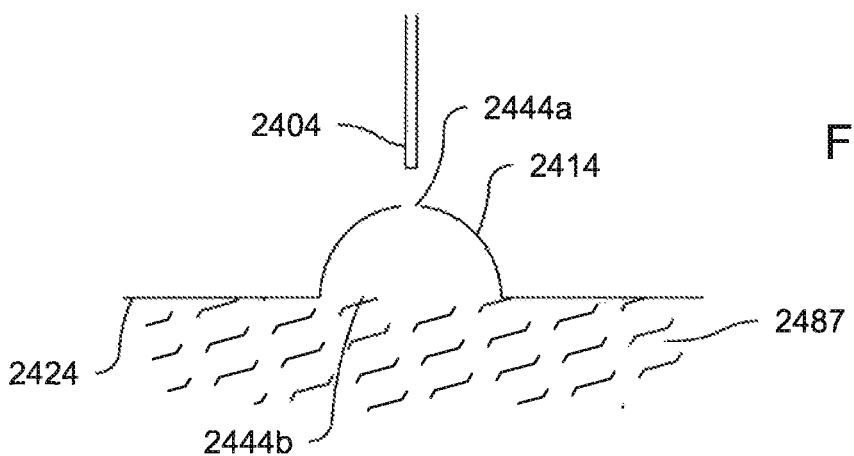

FIGS. 24A-24C are schematic illustrations of a needle safeguarding mechanism in accordance with an embodiment of the current invention. In some embodiment, a base includes a skin contact surface 2424. Optionally the base may also include an indentation 2414. Optionally, in some states a needle 2404 may be completely retracted into a housing of the device. For example, as illustrated in FIG. 24C, needle 2404 may be retracted behind base 2424 including indentation 2414. Optionally in an intermediate state, needle 2404 may project out from the inside of the housing to outside the housing through an opening 2444a of the base, but remain protected inside indentation 2414 on the outside of the housing, for example as illustrated in FIG. 24A. Optionally, in a fully extended state (for example as illustrated in FIG. 24B, the needle may extend out beyond skin contact surface 2424 and into a skin 2487 of a subject.

In some embodiments, an injector may have a preactivated and/or a primed state with needle 2404 in an intermediate position (for example as illustrated in FIG. 24A). For example, in a preactivated state, a tip of needle 2404 may be protected inside indentation 2414. Optionally in the preactivated state the needle tip may be further protected by an adhesive cover that covers the gap in skin contact surface 2424 over indentation 2414. Alternately or additionally, a needle may initially be covered by another needle cap. For example, a conventional tubular needle cover may be positioned over the needle. Optionally, the needle cap may be pulled off before use. Optionally the device is primed by removing the adhesive cover and/or needle cap and placing contact surface 2424 against skin 2487.

In some embodiments, the needle may be extended out of indentation 2414 into a subject in an activated state (for example as illustrated in FIG. 24B). For example, while the needle 2404 remains inside skin 2487, needle 2404 may be used to inject a drug into the subject.

In some embodiments, at the end of the activated state, needle 2404 may be retracted. For example, when drug discharge ends and/or when the device is removed from skin 2487, needle 2404 is retracted to a fully retracted position, for example as illustrated in FIG. 24C.

In some embodiments, needle 2404 may be in a fully retracted position before injection. In some embodiments, needle 2404 may be retracted to an intermediate position after injection.

In various embodiments, an indentation may have various geometries. For example an indentation may be semi-spherical and/or conical and/or semi ovoid and/or irregular in shape. For example an indentation may have one or more axis of symmetry. In some embodiments, an indentation may intersect an edge of the device and/or be open one or more sides. Optionally the depth of an indentation (for example the height of indentation 2414 in the direction of the axis of needle 2404) may range between 0.1 mm to 1 mm and/or 1 mm to 3 mm and/or 3 mm to 8 mm and/or more than 8 mm. The a width of an opening 2444b of indentation 2414 at a skin contact surface may range for example between 0.1 to 1 mm and/or between 1 to 5 mm and/or between 5 to 10 mm and/or from 10 to 30 mm and/or more. The a width of a needle hole (for example opening 2444a and/or 944) may range for example between 0.1 to 1 mm and/or between 1 to 5 mm and/or between 5 to 10 mm and/or from 10 to 30 mm and/or more.

Figure 25A:
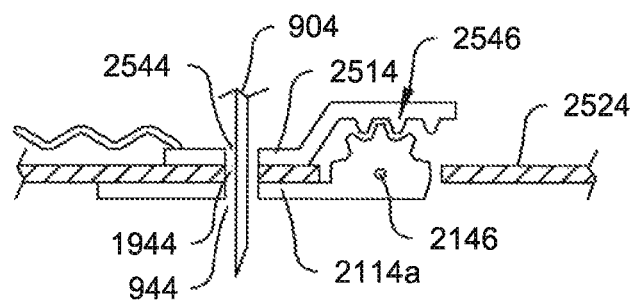
FIGS. 25A and 25B illustrate a sliding needle shield in accordance with an embodiment of the current invention.
Figure 25B:
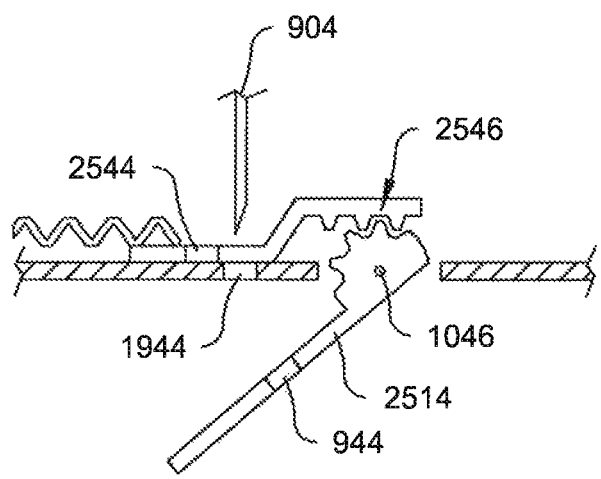

FIGS. 25A-25B are schematic illustrations of a rack and pinion needle safeguarding mechanism in accordance with an embodiment of the present invention. Optionally, during injection an opening 2544 in a sliding shield 2514 is aligned with an opening 1944 in a base 2524 of a device. For example, a rack and pinion system 2546, optionally including a one way ratchet, slides shield 2514 when a pivoting shield 2514 opens (for example when the device is removed from the skin of a user) shield 2514 slides dis-aligning openings 1944 and 2544 and/or locking needle 904 into a housing. In some embodiments a rack and pinion system may unlock a needle before deployment and/or close onto (to bend and/or twist and/or break a needle after drug discharge).

Figure 26A:
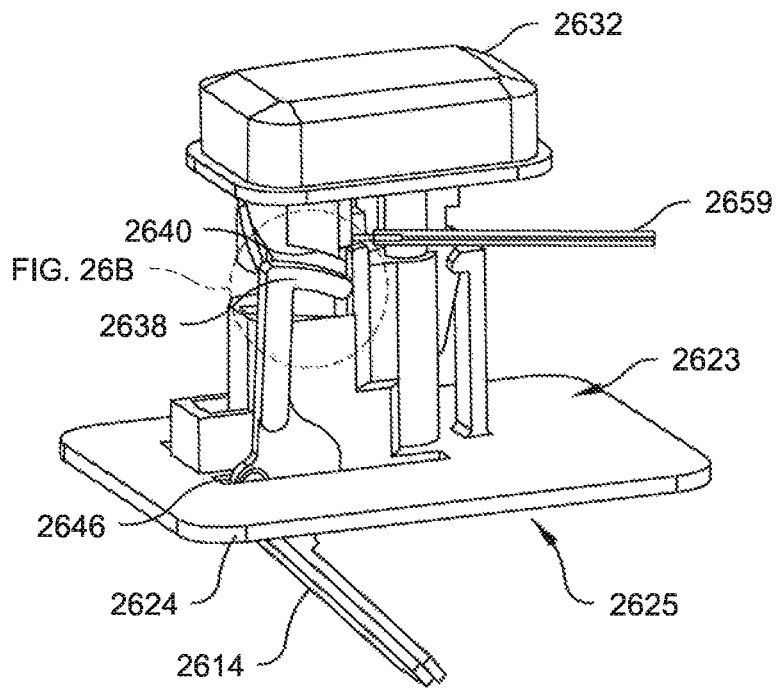
FIG. 26A is a perspective view of a needle mechanism in a preactivated locked state in accordance with an embodiment of the current invention.
Figure 26B:
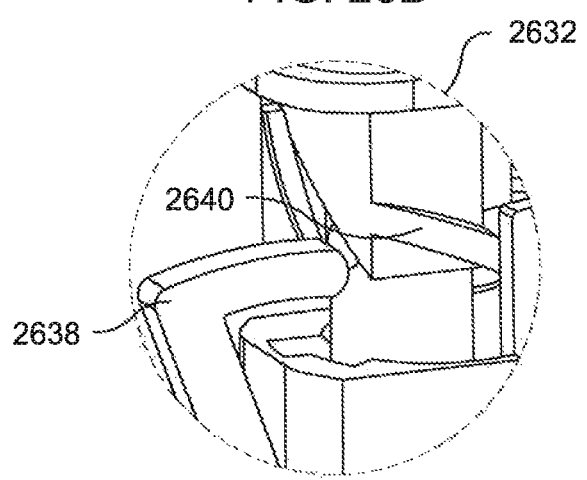
FIG. 26B is a perspective view of a needle mechanism in a primed unlocked state in accordance with an embodiment of the current invention.

FIGS. 26A, 26B and 26C illustrate an exemplary embodiment of a needle mechanism in accordance with an embodiment of the present invention. Optionally a needle mechanism has redundant protection. For example, a needle shield may protect a needle tip from becoming a stick hazard. Alternatively or additionally, the needle tip may be retracted to a protected location. Alternatively or additionally, a sensor may prevent extension of needle until the device has been properly primed and/or positioned on an injection zone. Alternatively or additionally, a needle shield may protect (for example by shielding) the needle tip when the needle is extended. Alternatively or additionally, the needle tip may be retracted to a protected location when the needle shield is compromised. In some embodiments, a single part may serve multiple functions. For example, a needle shield may also serve as a sensor for facilitating extension and/or retraction of the needle.

FIG. 26A is a perspective view of a needle mechanism in a preactivated locked state in accordance with an embodiment of the present invention (optionally as described for example in FIG. 6 state 622). Optionally a hollow needle 2604 (for example as illustrated in FIG. 26C) is connected on one end to a drug reservoir (for example by a flexible tube 2659 alternatively or additionally a needle may be directly attached to a reservoir for example to a syringe). The needle 2604 optionally includes a sharp tip 2609 at an end opposite from the reservoir.

In some embodiments, depressing an activation button 2632 causes needle tip 2609 to extend out of the device. For example, when the device is in the preactivated state and/or when the device is attached to the skin of a subject the activation. For example, activation may include the needle tip 2609 piercing the skin of a subject and/or the hollow of needle 2604 may form a fluid pathway between the drug reservoir and the subject.

In some embodiments, in the preactivated, locked state, tip 2609 is shielded by a housing of the device. For example, tip 2609 is supported on an inner side 2623 of a wall (for example base 2624) of the housing. Optionally a safety latch 2638 of a skin sensor 2614 locks button 2632 in an un-depressed position inhibiting premature extension of tip 2609 and/or preventing a stick hazard. For example, when skin sensor 2614 is extended out from an outer surface 2625 of base 2624, latch 2638 may block movement of an interference element 2640 and/or latch 2638 may block depressing of button 2632.

FIG. 26B is a perspective view of a needle mechanism in a primed unlocked state in accordance with an embodiment of the present invention (optionally as described for example in FIG. 6 state 614). In some embodiments, when the outer surface 2625 of base 2624 is pushed against the skin of a subject (for example at an injection site), sensor 2614 is pushed upwards towards base 2624. Optionally, pushing sensor 2614 towards base 2624 causes sensor 2614 and/or latch 2638 to pivot around a hinge 2646. Pivoting optionally moves latch 2638 out of the way of interference element 2640 and/or facilitates depressing button 2632.

In some embodiments, depressing button 2632 triggers an automatic needle insertions mechanism for example as illustrated in FIG. 26C to FIG. 28C. Alternatively or additionally, force on button 2632 directly pushes needle 2626. For example, needle 2604 may be rigidly attached to button 2632 and/or move therewith.

FIG. 26C is a cutaway view of a needle mechanism in accordance with an embodiment of the current invention. In some embodiments, a needle mechanism may include one or more stored energy sources. Stored energy may be used for needle extension, protection and/or for sensing. Optionally, one or more components of a needle retraction system will serve different functions depending on the state of the system. Optionally, the needle retraction system movable mounts needle 2604 a housing (for example a base 2624). For example, the needle mechanism may movably connect needle 2604 to base 2624. For example, a tip 2609 of a needle 2604 may move longitudinally with respect to the housing. For example, a sharp tip 2609 may move through a needle hole 2644 to be exposed and/or protected, for example as described herein below.

In some embodiments, needle extension, retraction and/or shielding may be driven by a stored energy source. For example, a compression spring 2618 may drive the needle extension. For example, a second counter compression spring 2605 may drive needle retraction. For example, a torsion spring 2647 may drive deployment of a skin sensor 2614. Optionally sensor 2614 may serve multiple functions at different states of the system. For example, sensor 2614 may act as a skin sensor to unlock needle extension when the device is placed on an injection site. For example, sensor 2614 may act as a needle shield protecting a sharp needle point after the end of drug delivery and/or while the needle is extended. For example, sensor 2614 may act as a trigger needle for retraction. Optionally, a single stored energy device may drive multiple movements. For example, a single torsion spring may drive a wheel wherein a first half turn causes needle extension and a second half turn causes needle retraction and/or a compression spring may pull a pin along a track which moves the needle first to the extended position and subsequently back to the retracted position.

In some embodiments, sensor 2614 may be mechanically interlocked with a needle extension mechanism (for example button 2632 as illustrated for example in FIGS. 26A and 26B). For example, the interlock may unlock a needle extension mechanism when the injector in a locked preprimed state is placed on an injection site, for example as explained in reference to FIGS. 26A and 26B.

In some embodiments, sensor 2614 may shield a needle. For example, after drug delivery and/or when the delivery device is removed from the injection site, sensor 2614 may be deployed to shield a needle (as illustrated for example in FIGS. 29A-29C and/or in connection to a shielded state in FIG. 5 and/or in connection to a partially protected state and/or in connection to FIGS. 13A-13C).

Figure 27A:
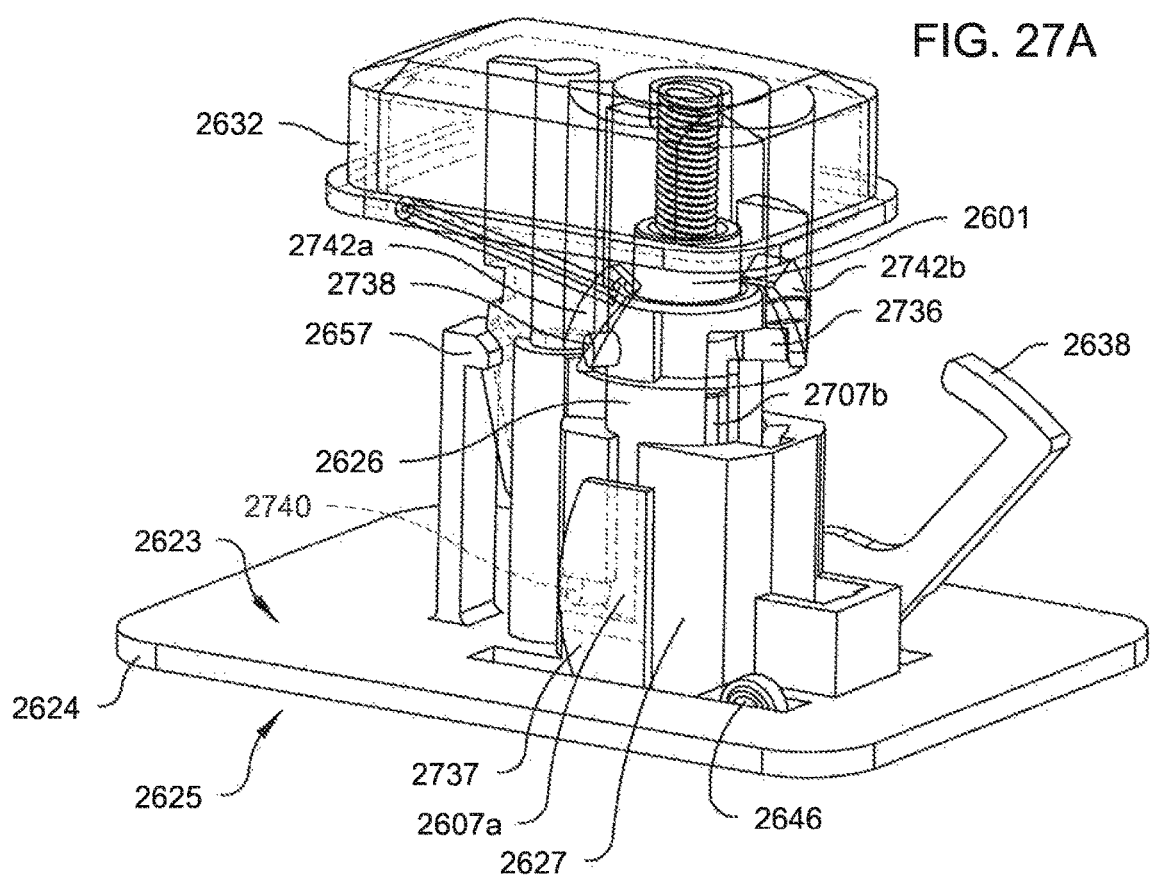
FIGS. 27A to 27C illustrate a needle assembly in a primed state in accordance with an embodiment of the current invention.
Figure 27C:
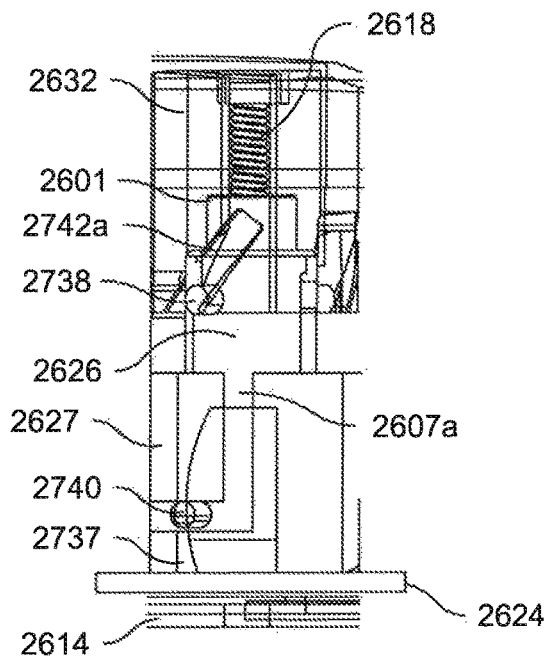
Figure 27B:
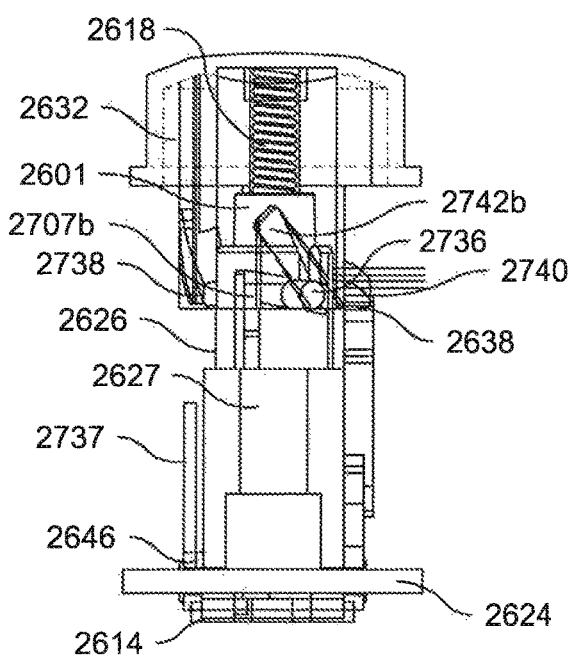

FIGS. 27A to 27C illustrate a needle assembly in a primed state in accordance with an embodiment of the current invention. In some embodiments, a skin contact surface on an outer surface 2625 of the injector is adhered to the skin of a subject. Optionally, placing the skin contact surface onto the skin forces pushes sensor 2614 and/or pivots it upward around pivot 2646. Optionally, sensor against moves upward until is rests against and/or is flush to outer surface 2624. Optionally, as sensor 2614 pivots upward, safety latch 2638 pivots away from activation button 2632, freeing button 2632 to move downward. Optionally, freeing button 2632 to move downward, primes the device.

FIG. 27B illustrates a needle insertion mechanism in a primed state in accordance with an embodiment of the present invention. In some embodiments, needle insertion may be powered by stored energy in the device. For example, spring 2618 pushes downward on a needle holder 2601 rigidly connected to the needle 2604. In the primed state, the needle 2604 is optionally locked in a retracted position by a pin 2736 in a track 2707b. A slanted track 2742b in button 2632 optionally controls the horizontal position of pin 2736. As button 2632 is depressed (vertically downward) pin 2736 is optionally forced by slanted track 2742b leftward (e.g. by rotating needle holder 2601).

FIG. 27C illustrates a needle retraction mechanism in a primed state in accordance with an embodiment of the present invention. In some embodiments, needle retraction may be powered by stored energy in the device. For example, spring 2605 (for example as illustrated in FIG. 26C) pushes upward on a retraction slider 2626. Slider 2626 optionally includes two pins 2738 and 2740. In the primed state, slider 2626 is optionally locked in a pre-retracted position by a pin 2740 in a track 2707a. A slanted track 2742b in button 2632 optionally controls the horizontal position of pin 2736. As button 2632 is depressed (vertically downward) a second pin 2738 is optionally forced by slanted track 2742a rightward (rotating slider 2626 and/or pin 2740 rightward).

Figure 28A:
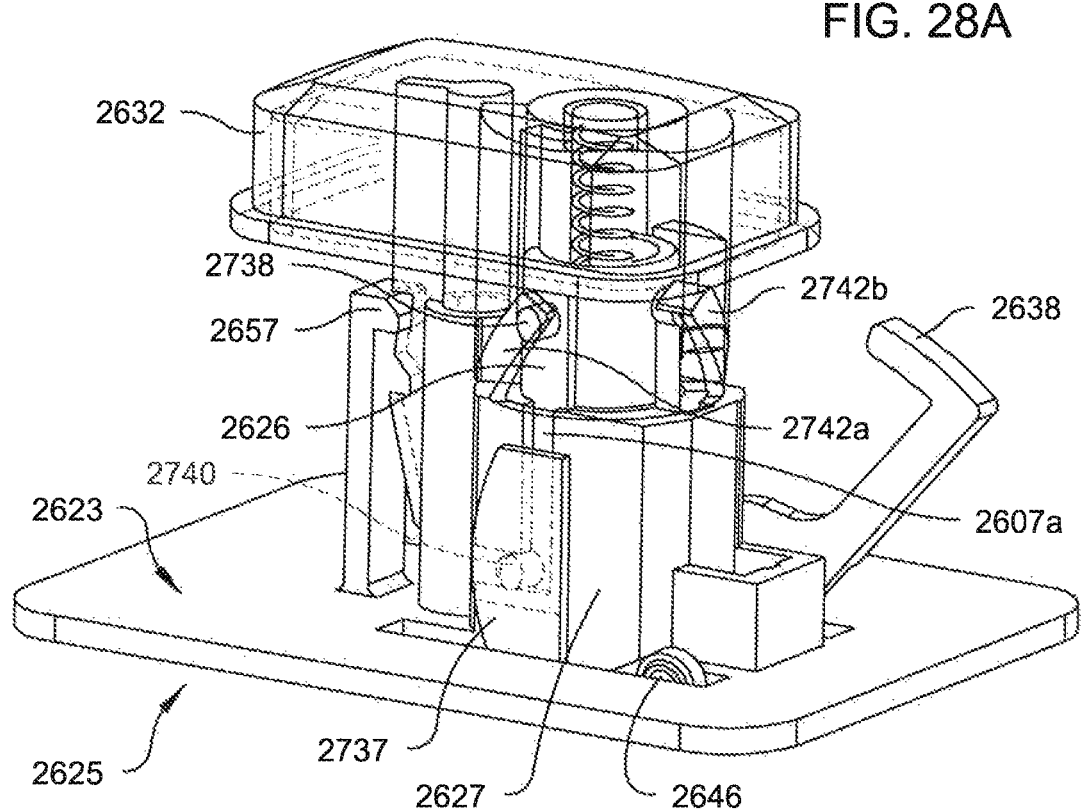
FIGS. 28A to 28C illustrate a needle assembly in an activated state in accordance with an embodiment of the current invention.
Figure 28C:
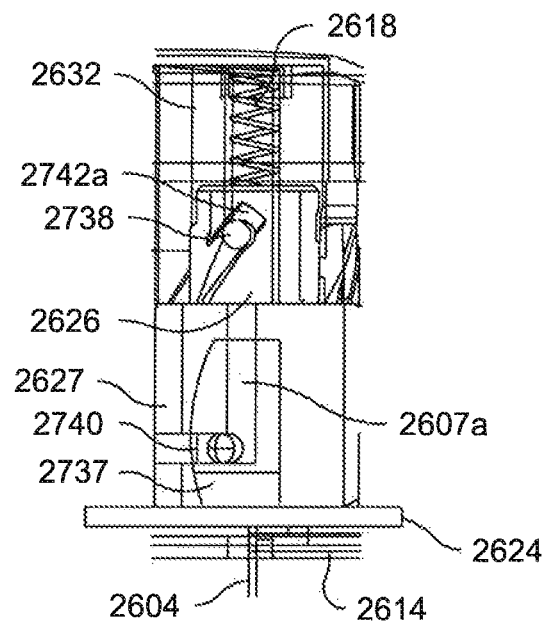
Figure 28B:
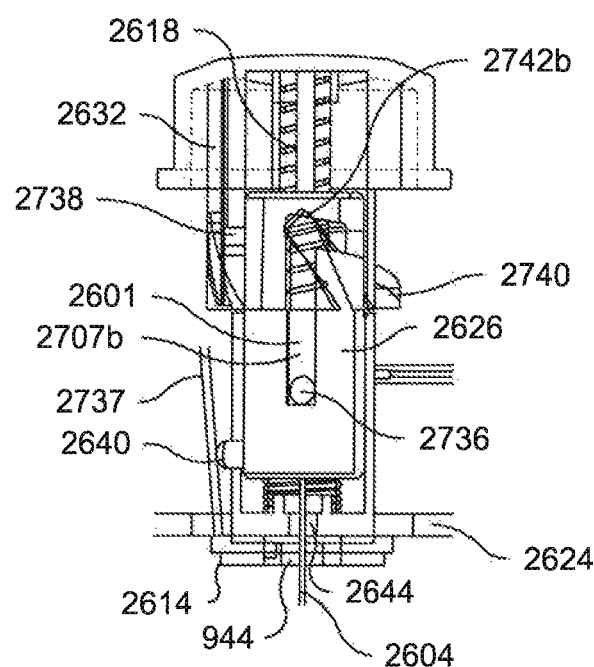

FIGS. 28A to 28C illustrate a needle assembly in an activated state in accordance with an embodiment of the current invention. In some embodiments, a user depresses an activation button 2632 to activate the device. For example, as illustrated in FIG. 28B, when button 2632 is fully depressed, track 2742b has forced pin 2736 leftward until it has reached a vertical portion of track 2707b. In some embodiments, once pin reaches the vertical portion of track 2707b, it is free to move downward, unlocking downward movement of needle holder 2601. Optionally, once unlocked needle holder 2601 and needle 2604 are pushed downward by expanding spring 2618. Downward movement optionally extends sharp tip 2609 (illustrated for example in FIG. 26C) of needle 2604 out openings 944 and 2644 in base 2624 and/or shield 2614 respectively.

In some embodiments, needle tip 2609 is extended out of opening 2644 of base 2624 and/or opening 944 of sensor 2614 while outer surface 2625 of base 2624 is adhered to a skin of a subject. Optionally, an opposite end of needle 2604 remains in fluid connection with a medicine reservoir inside the housing of the delivery device. For example the hollow of needle 2604 becomes a fluid path for injecting a drug from the reservoir into the subject.

FIG. 28C illustrates a needle retraction mechanism in an active state in accordance with an embodiment of the current invention. Optionally, when the device is activated (for example by depressing activation button 2632) the retraction mechanism is moved to an armed mode, ready to retract. For example, pin 2740 is moved close to its unlocked position, the vertical portion of track 2707a. Alternatively or additionally, a retraction mechanism may be armed and/or further armed to a ready to retract configuration when the device is removed from the skin for example when skin sensor 2614 is deployed (for example as illustrated in FIGS. 29A-C).

In some embodiments, a lock of the retraction mechanism is a mechanically linked to skin sensor 2614. For example, pin 2740 interferes with an arm 2737 of skin sensor 2614. For example, in FIG. 28B it is seen that in the active state, pin 2640 contacts a arm 2737 of sensor 2614 and/or elastically deforms arm 2737 outward.

Figure 29A:
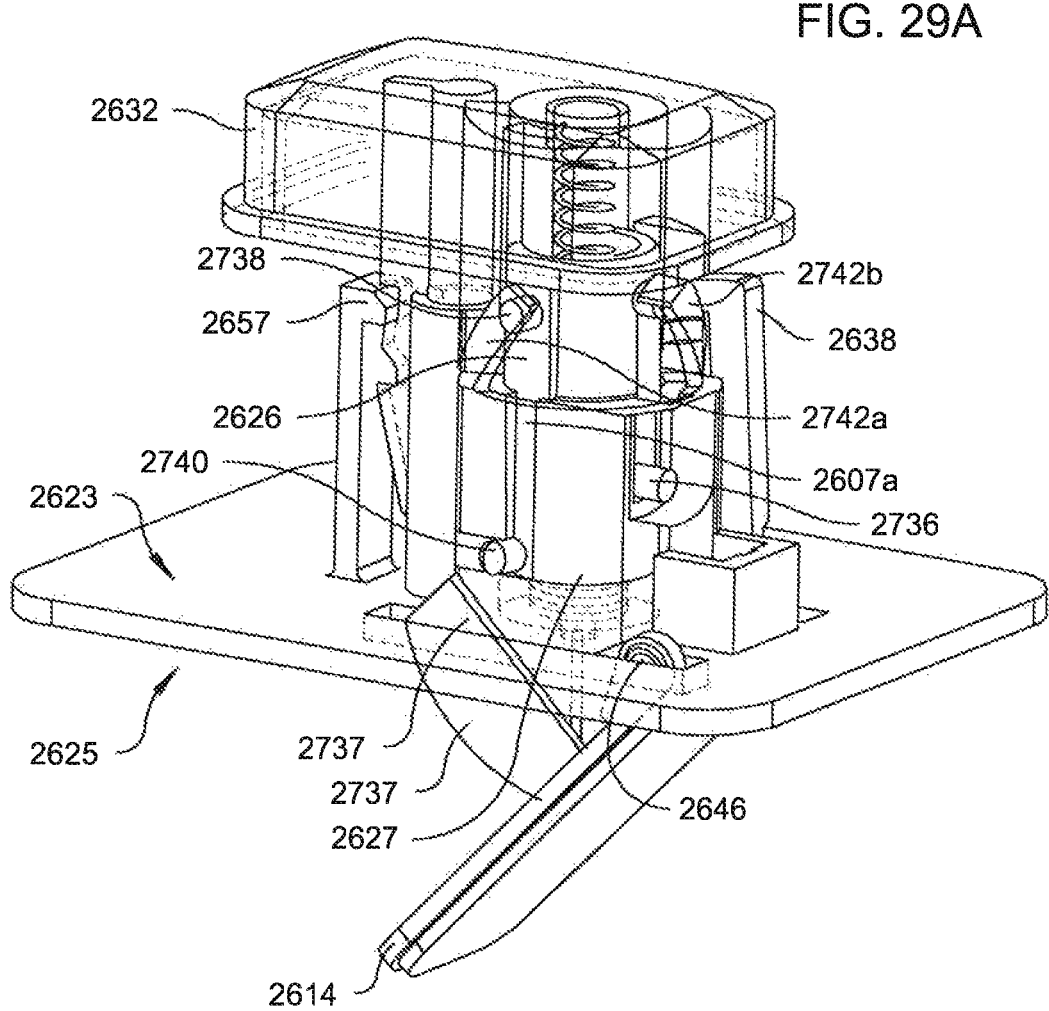

FIGS. 29A-29C illustrate a needle retraction mechanism in a partially protected state in accordance with an embodiment of the current invention (for example as described in state 605 of FIG. 6 and/or step 308 of FIG. 3). Optionally, in the partially protected state, needle 2604 remains in an extended state and/or sensor 2614 is deployed to shield sharp tip 2609. Optionally, a skin sensor is deployed when a delivery device is removed from delivery site. For example, sensor 2614 pivots around pivot 2646 such that sensor 2614 covers the sharp tip 2609 that passes through aperture 944 which is moved out of alignment with sharp tip 2609.

Figure 30A:
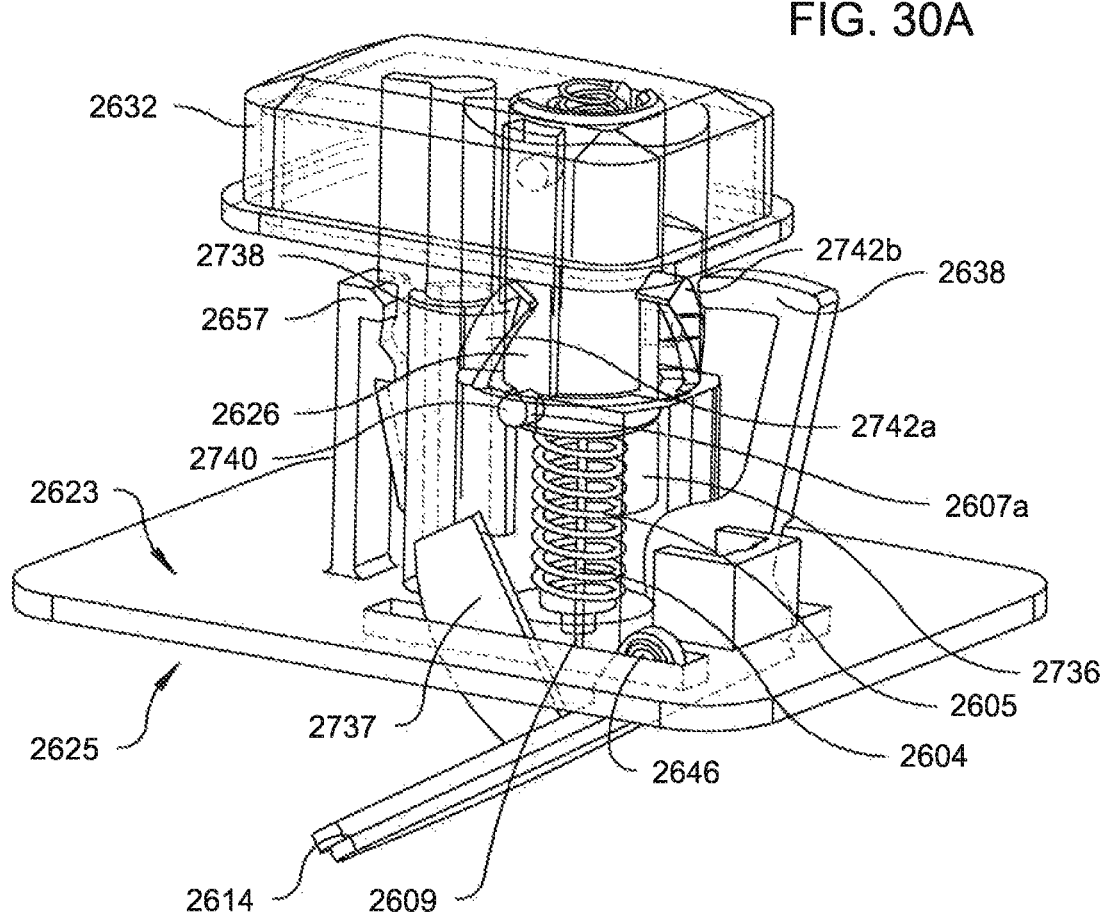
Figure 30B:
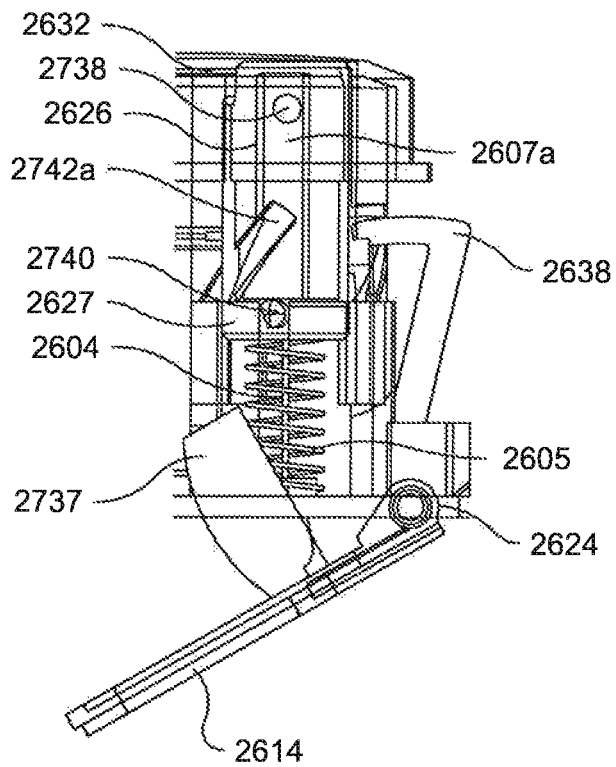
Figure 30C:
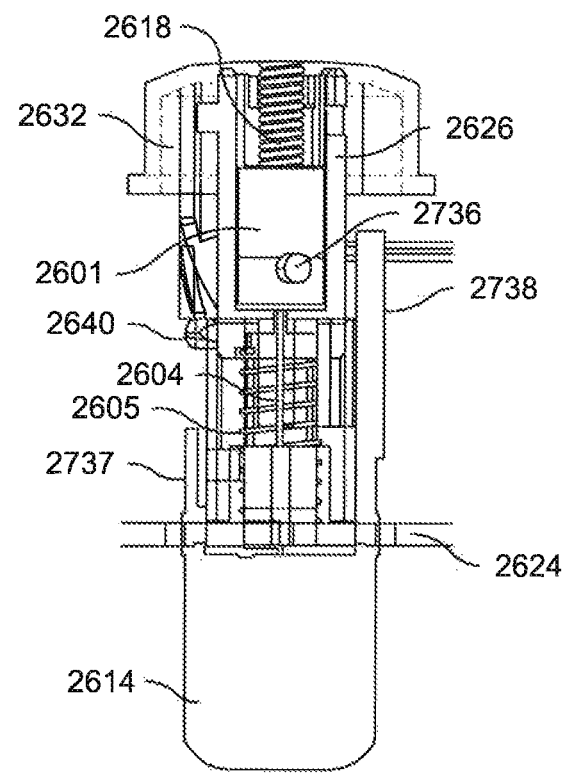

FIGS. 30A-30C illustrate a needle retraction mechanism in a fully protected state in accordance with an embodiment of the current invention (for example as described in state 604 of FIG. 6 and/or step 305 of FIG. 3). Optionally, in the fully protected state sharp tip 2609 has retraced behind outer surface 2625 (for example into opening 2644). Alternatively or additionally, in the fully protected state a sharp tip retracts behind the surface 2625.

In some embodiments, when a needle shield is compromised, a needle is retracted. For example, when skin sensor 2614 is moved from the partially protected state shielding sharp tip 2609 towards housing 2624 (for example, pivoting upward around pivot 2646) arm 2737 pushes pin 2740 into the vertical portion of track 2707a unlocking needle retraction slider 2626. When slider 2626 is unlocked, it is optionally moved automatically away from opening 2644. For example, spring 2605 expands pushing up slider 2626, needle holder 2601 and/or needle 2604. Optionally, the upward movement also moves sharp tip 2609 into the retracted position and/or a fully protected state. Alternatively or additionally, retraction may not be automatic. For example retraction may be driven by a force, for example an upward force of sensor 2614 on needle tip 2609 and/or holder 2601 and/or slider 2626.

It is expected that during the life of a patent maturing from this application many relevant technologies will be developed and the scope of the terms are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A needle insertion and retraction mechanism for an injector having a housing with a base defining an opening, the needle insertion and retraction mechanism comprising:
    an injection needle mounted to a needle retainer, the needle retainer being linearly slidable along a first track between a retracted position, in which a tip of the injection needle is within the housing, and an extended position, in which the tip of the injection needle projects outward from the housing through the opening;
    a shield defining a needle aperture and having an interference element extending therefrom, the shield being movable relative to the housing between a deployed position, in which the needle aperture is misaligned with the injection needle and a withdrawn position, in which the needle aperture is aligned with the injection needle;
    a retraction spring engaged with the needle retainer at one end and engaged with the shield at an opposing end, the retraction spring applying a first biasing force to the needle retainer in a first direction and a second biasing force to the shield in a second direction;
    a driver engageable with the needle retainer, the driver being linearly slidable along, and rotatable about, a second track, the driver being slidable by a main spring, the main spring providing a biasing force in a direction opposite the first biasing force of the retraction spring; and
    an activation button depressible to rotate the driver about the second track into engagement with the needle retainer;
    wherein:
    in a pre-activation state of the insertion and retraction mechanism before the injector is placed on a skin surface of a patient, the second biasing force of the retraction spring orients the shield in the deployed position, in which the interference element blocks downward movement of the activation button, locking the needle retainer and the injection needle in the retracted position, and the retraction spring is in an expanded configuration and the main spring is in a compressed configuration;
    in a primed state of the insertion and retraction mechanism, the injector is placed on the skin surface of the patient and the shield is moved to the withdrawn position thereof, in which the retraction spring is partially compressed and the interference element ceases blocking downward movement of the activation button;

in an activation state of the insertion and retraction mechanism, the activation button is depressed, engaging the driver with the needle retainer and freeing the main spring to push the driver and the engaged needle retainer and the injection needle into the extended position, thereby further compressing the retraction spring; and in an intermediate state of the insertion and retraction mechanism after the injector is removed from the skin surface of the patient, the driver is disengaged from the needle retainer, and the retraction spring partially expands and returns the shield to the deployed position, in which the shield restricts the needle retainer from returning to the retracted position and covers the tip of the injection needle, and wherein subsequent contact with the shield toward the withdrawn position releases the needle retainer, whereby the retraction spring further expands and retracts the needle retainer and injection needle.

2. The mechanism of claim 1, wherein the tip of the injection needle is positioned between said shield and said housing in the intermediate state.

3. The mechanism of claim 1, wherein said contact with the shield toward the withdrawn position in the intermediate state comprises exerting a force of at least 1 N on said shield.

4. The mechanism of claim 3, wherein said force is at least partially directed toward said housing.

5. The mechanism of claim 1, wherein said shield is pivotally mounted on said housing and in the deployed position said shield is pivoted away from said housing.

6. The mechanism according to claim 1, wherein said shield is flush with said housing in the withdrawn position.

7. The mechanism of claim 1, wherein said shield is biased toward said deployed position by the retraction spring.

8. The mechanism of claim 1, wherein the retraction spring maintains the needle retainer in the retracted position at one end and the shield in the deployed position at the other end, in a fully expanded configuration of the retraction spring.

9. The mechanism of claim 1, further comprising a blocking element and wherein the driver includes a protrusion, and wherein, in the compressed configuration of the main spring, the protrusion of the driver is abutted by the blocking element, maintaining the main spring in the compressed configuration and inhibiting downward movement of the driver.

10. The mechanism of claim 9, wherein the activation button includes a wedge element configured to transform a force in a downward direction on the button to a force in a sideways direction on the driver.

11. The mechanism of claim 10, wherein depressing the activation button in the activation state pushes the wedge against the protrusion of the driver and transmits a lateral force onto the protrusion, causing a torque on the driver which rotates the driver around the second track, disengaging the protrusion from the blocking element and freeing the main spring.

12. The mechanism of claim 11, wherein the driver comprises an element and the needle retainer comprises a corresponding interference element, and wherein rotating the driver linearly aligns the element of the driver with the corresponding interference element of needle retainer, thereby linking linear downward movement of the driver and the needle retainer.

* * * * *